United States Patent
Morris

(10) Patent No.: US 6,306,099 B1
(45) Date of Patent: Oct. 23, 2001

(54) METHOD OF MEASURING RESIDUAL LUNG VOLUME IN INFANTS

(75) Inventor: Mohy G. Morris, Little Rock, AR (US)

(73) Assignees: Board of Trustees of the University of Arkansas; Arkansas Children's Hospital Research Institute, Inc., both of Little Rock, AR (US)

(*) Notice: Subject to any disclaimer, the term of this patent is extended or adjusted under 35 U.S.C. 154(b) by 0 days.

(21) Appl. No.: 09/506,147

(22) Filed: Feb. 17, 2000

(51) Int. Cl.[7] .................................................. A61B 5/08
(52) U.S. Cl. ........................................ 600/529; 600/532
(58) Field of Search ................................. 600/529, 532, 600/531, 533, 537, 536, 538, 539, 540, 541, 542, 543, 204.22, 204.23, 204.26, 204.15; 73/23.3

(56) References Cited

U.S. PATENT DOCUMENTS

| | | | |
|---|---|---|---|
| Re. 28,513 | * 8/1975 | Suzuki et al. | 600/538 |
| 4,307,730 | * 12/1981 | Korn | 600/541 |
| 4,333,476 | 6/1982 | Downing, Jr. . | |
| 4,796,639 | 1/1989 | Snow et al. . | |
| 5,119,825 | 6/1992 | Huhn . | |
| 5,513,647 | 5/1996 | Castile . | |
| 5,540,233 | * 7/1996 | Larsson et al. | 600/538 |
| 5,957,128 | 9/1999 | Hecker et al. . | |
| 6,139,506 | * 10/2000 | Heinonen | 600/532 |

OTHER PUBLICATIONS

Hammer, et al., "Total lung Capacity by $N_2$ Washout from High and Low Lung Volumes in Ventilated Infants and Children," American Journal of Respiratory and Critical Care Medicine, vol. 158, 1988, pp. 526–531.

Feher, et al., "Flow limitation in normal infants: a new method for forced expiratory maneuvers from raised lung volumes," Journal of Applied Physiology, vol. 80, 1996, pp. 2019–2025.

McCoy, et al., "Functional Residual Capacity (FRC) Measurements by Plethysmography and Helium Dilution in Normal Infants," Pediatric Pulmonology, vol. 19, 1995, pp. 282–290.

Morris, M., "The open circuit nitrogen washout technique for measuring the lung volume in infants: methodological aspects," Thorax, vol. 54, 1999, pp. 790–795.

Morris, M., "A novel non–invasive technique for measuring the residual lung volume by nitrogen washout with rapid thoracoabdominal compression in infants," Thorax, 1999, vol. 54, pp. 874–883.

Hayden, et al., "Methacholine Responsiveness Using the Raised Volume Forced Expiration Technique in Infants," American Journal of Respiratory and Critical Care Medicine, vol. 155, 1997, pp. 1670–1675.

(List continued on next page.)

*Primary Examiner*—Robert L. Nasser
*Assistant Examiner*—Navin Natnithithadha
(74) *Attorney, Agent, or Firm*—Ray F. Cox, Jr.

(57) ABSTRACT

A method of measuring residual lung volume (RV) in infants by washout of nitrogen or other inert gas, using a compression jacket for rapid thoracoabdominal compression (RTC). RTC is performed from a raised lung volume ($V_{30}$) to an airway opening pressure. The jacket pressure ($P_j$) (range 65–92 cm $H_2O$) which generates the highest forced expiratory volume is used during the RV maneuver. The infant is manually hyperventilated to briefly inhibit the respiratory drive. RTC is initiated during the last passive expiration. By measuring the volume of nitrogen expired after end-forced expiratory switching of the inspired gas from a breathable mixture containing an inert gas to 100% oxygen while RTC is maintained during the post-expiratory pause, RV is calculated.

7 Claims, 10 Drawing Sheets

OTHER PUBLICATIONS

Hayden, et al., "Influence of Driving Pressure on Raised-volume Forced Expiration in Infants," American Journal of Respiratory and Critical Care Medicine, vol. 156, 1997, pp. 1876–1883.

Turner, et al., "A New Technique to Generate and Assess Forced Expiration from Raised Lung Volume in Infants," American Journal of Respiratory and Critical Care Medicine, vol. 151, 1995, pp. 1441–1450.

Morris, M., Abstract, "A New Technique to Measure Residual Volume (RV) by Nitrogen Washout with Rapid Thoracoabdominal Compression (RTC) in Infants," 1995 ALA/ATS International Conference, Apr. 27, 1999.

Morris, M., Draft Manuscript, "A novel noninvasive technique to measure the residual lung volume by nitrogen washout with rapid thoracoabdominal compression in infants," Submitted to Thorax on Dec. 29, 1998.

* cited by examiner

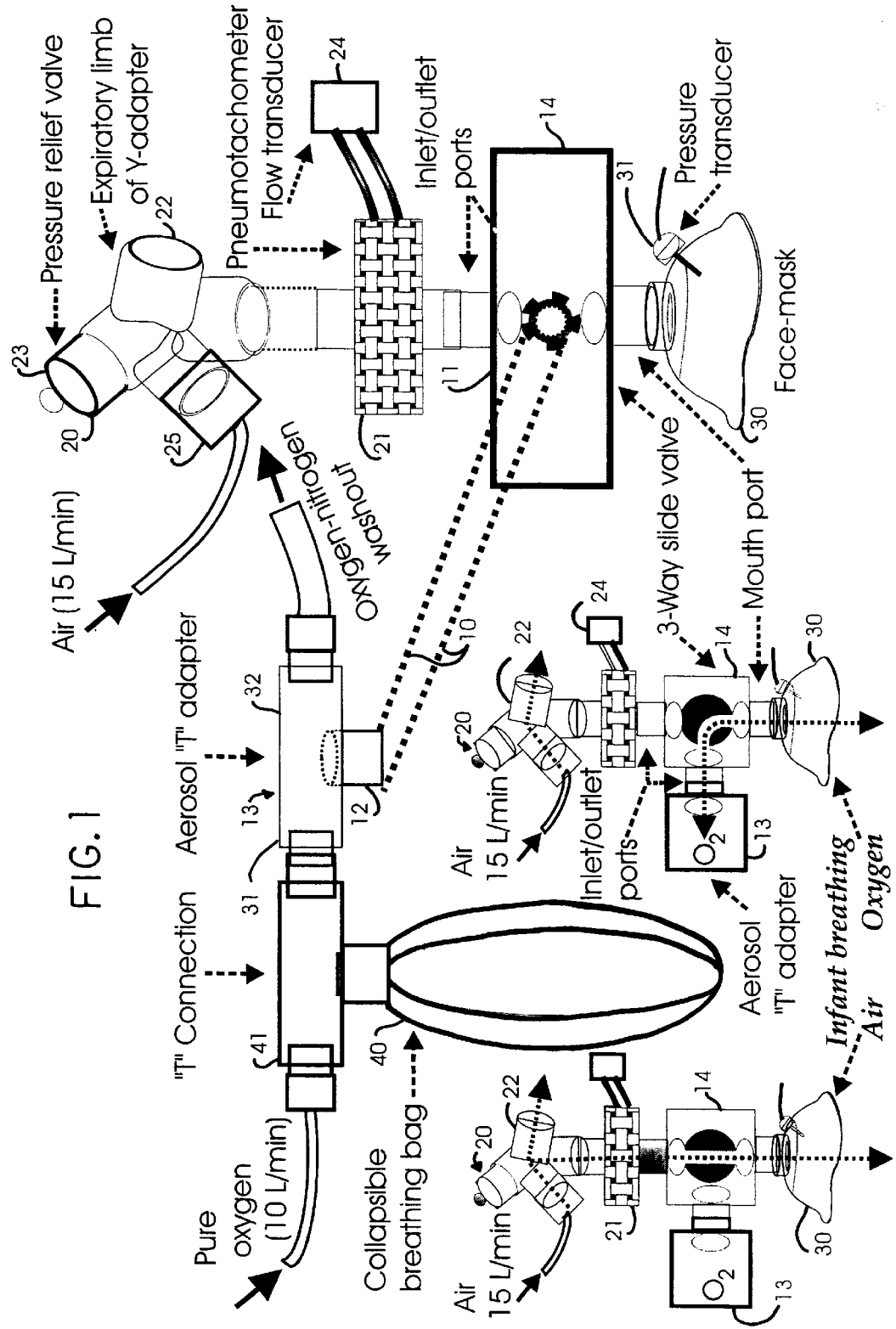

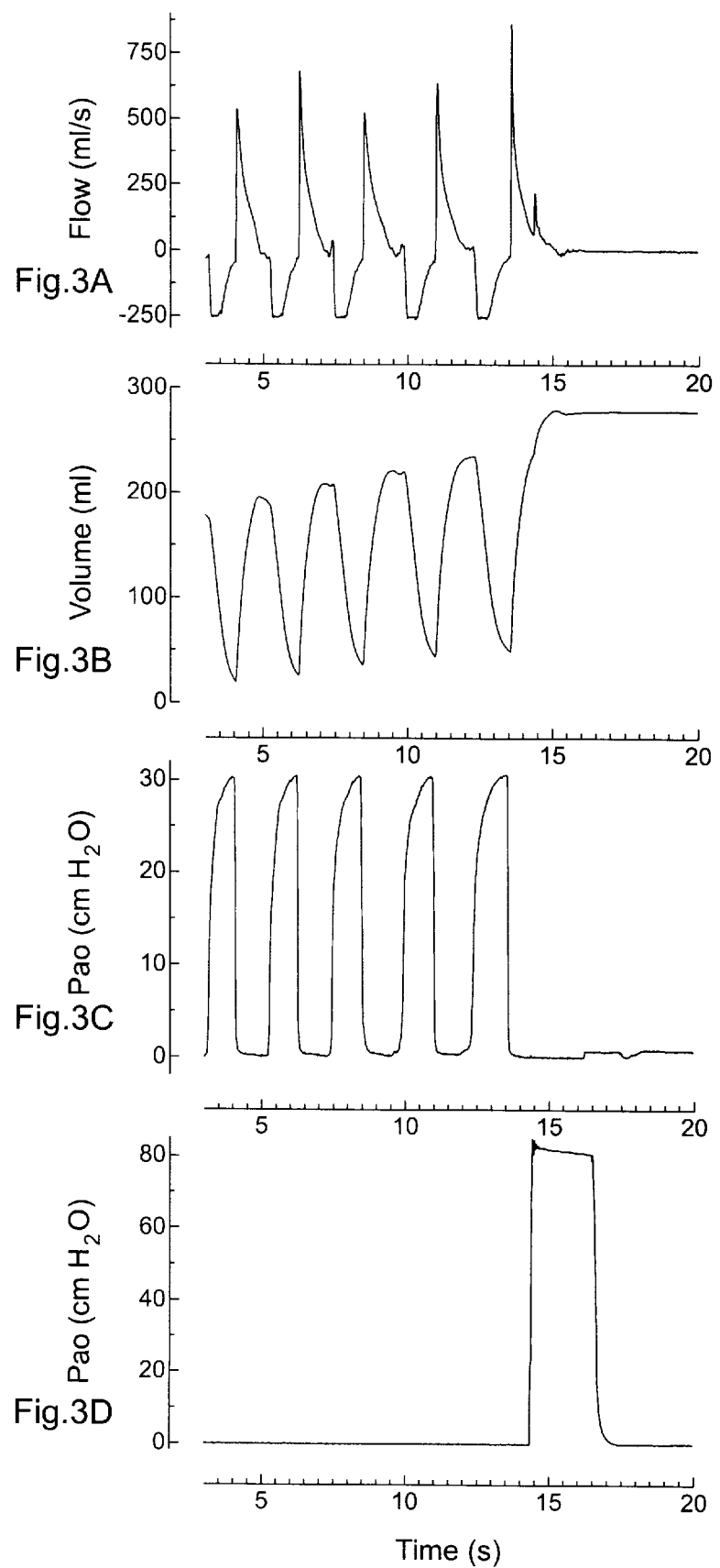

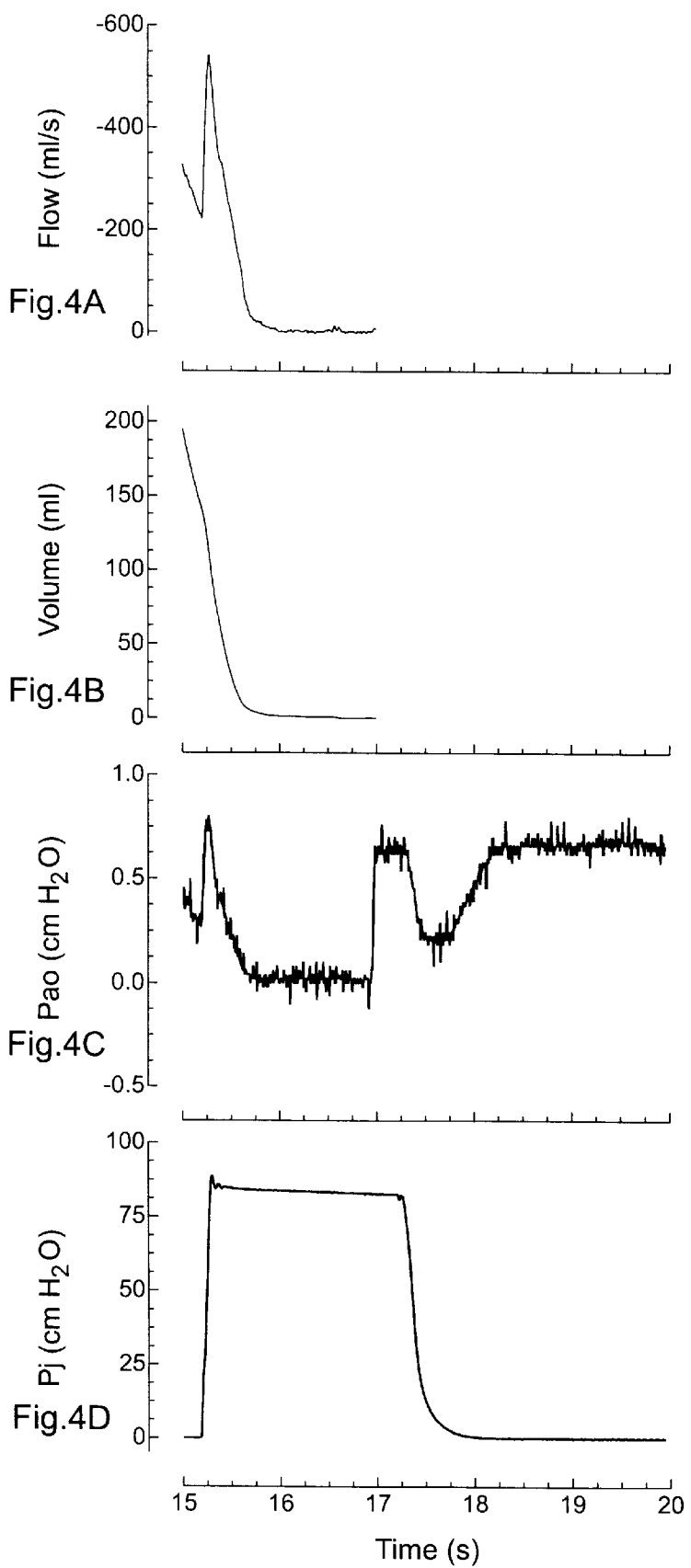

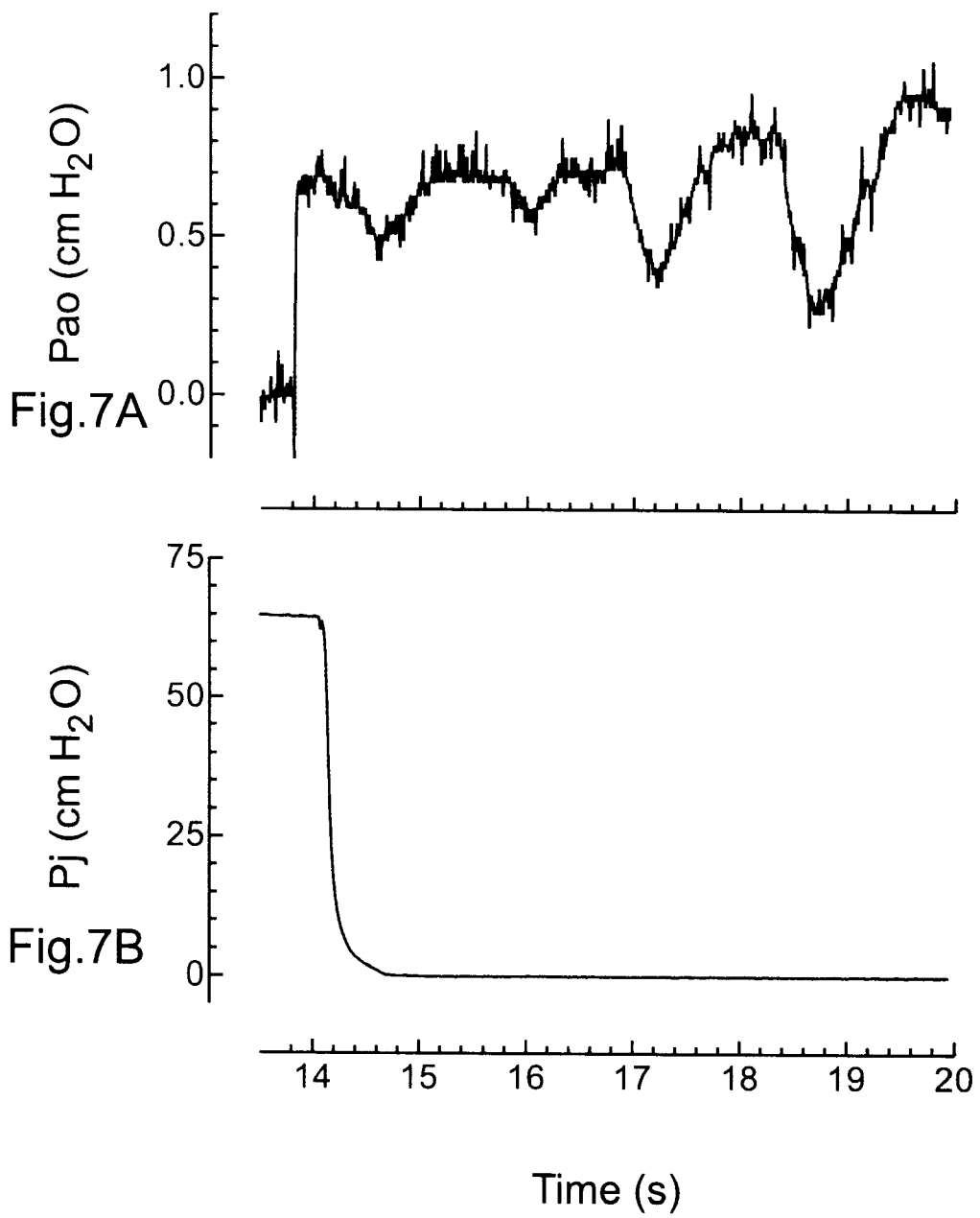

METHOD OF MEASURING RESIDUAL LUNG VOLUME IN INFANTS

BACKGROUND OF THE INVENTION

Objective assessment of lung function has provided valuable insights into the normal process of growth and development of infant lungs and airways. It is also an important component in the diagnosis and management of respiratory diseases and disorders, and is essential to our understanding of their acute or chronic effects and eventually our ability to prevent or minimize these effects (American Thoracic Society/European Respiratory Society. Respiratory mechanics in infants: physiological evaluation in health and disease. *Am Rev Respir Dis* 1993; 147: 474–96.).

The functional residual capacity (FRC), i.e., the volume of air in the lungs and airways at end-tidal expiration, is the only lung volume that is routinely measured in infants. (American Thoracic Society/European Respiratory Society. Respiratory mechanics in infants: physiological evaluation in health and disease. *Am Rev Respir Dis* 1993; 147: 474–96; Gaultier C. Lung volume in neonates and infants. *Eur Respir J* 1989; 2(Suppl 4: 130s–4s)). In infants, FRC is usually dynamically determined, in that young infants inspire before expiration ends passively. (LeSouëf PN, England S J, Bryan A C. Passive respiratory mechanics in newborns and children. *Am Rev Respir Dis* 1984; 129, 552–56.). Therefore, FRC is an unreliable volume landmark known to shift with many dynamic events, including the airway caliber (Maxwell D L, Prendiville A, Rose A, et al. Lung Volume changes during histamine-induced bronchoconstriction in recurrently wheezy infants. *Pediatr Pulmonol* 1988; 5,145–151), sleep state (Stark A R, Cohlan B A, Waggener T B, et al. Regulation of end-expiratory lung volume during sleep in premature infants. *J Appl Physiol* 1987; 62; 1117–23; Beardsmore C S, MacFayden U M, Moosavi S S, et al. Measurement of lung volume during active and quiet asleep in infants. *Pediatr Pulmonol* 1989; 7:71–77.) and the addition of dead space (Stick S M, Arnott J, Turner D J, et al. Bronchial responsiveness and lung function in recurrently wheezy infants. *Am Rev Respir Dis* 1991; 144, 1012–15). Previous measurements of other lung volumes such as the residual volume (RV); i.e., the volume of air remaining in the lung at the end of a forced expiration, and total lung capacity (TLC) either required invasive techniques or had an unacceptable reproducibility.

SUMMARY OF THE INVENTION

We have therefore developed a new technique to measure RV noninvasively by nitrogen washout in infants. It should be noted that although the preferred embodiment of the invention employs nitrogen, the invention is not so limited, and other inert gases, such as helium, are acceptable in the practice of the invention.

We have investigated the methodological aspects of our new technique and applied it to a group of infants who have cystic fibrosis (CF). The basic underlying concept of this investigation was the observation of an inhibition of the infant's respiratory drive when several rapid lung inflations preceded the performance of rapid thoracoabdominal compression (RTC) from a raised lung volume (RVRTC). Feher A, Castile R, Kisling J, et al. Flow limitation in normal infants: a new method for expiratory maneuvers from raised volume. *J Appl Physiol* 1996; 80 (6), 2019–25. This brief inhibition not only allowed the forced expiration by RTC to proceed, uninhibited by the infant's inspiratory effort, to residual volume, but also to be followed by a respiratory pause before the resumption of spontaneous respiration. Our working hypothesis was that by measuring the volume of nitrogen expired after end-forced expiratory switching of the inspired gas from room air to 100% oxygen while thoraco-abdominal compression was maintained during the post-expiratory pause, RV could be reliably estimated from the volume of expired nitrogen. In CF lung disease, the small airways are affected at an early stage, resulting in obstructive airflow limitations with consequent overinflation. (Davis P B. Pathophysiology of lung disease in cystic fibrosis. In: Davis P B, ed. *Cystic Fibrosis*. New York: Marcel Dekker, Inc, 1993: 193–218.). Hence, we think that measurement of RV could be more useful than FRC in investigating early air trapping due to small airway obstruction in CF. Therefore, the second aim of this study was to ascertain whether, in each infant, RV measurements would be reproducible and consistently lower than FRC.

We used a commercial system (PPU) designed to measure the functional residual capacity (FRC) {the volume of air remaining in the lung at the end of a tidal expiration} by the nitrogen washout technique. Using a custom-made system to induce a forced expiration, we used the PPU to measure the residual lung volume (RV) {the volume of air remaining in the lung at the end of a forced expiration}. FRC, the only lung volume to be routinely measured in infants, is an unreliable volume landmark. The present invention is the first noninvasive and reproducible measurement of RV that can be routinely used in infants.

Inherent to the new technique is the capability of measuring, noninvasively, and for the first time, the total lung capacity ($TLC_{30}$) at a raised lung volume ($V_{30}$) to an airway opening pressure ($P_{ao}$) of 30 cm $H_2O$. We measured it in three different ways. A computer-controlled system can be easily designed to perform automatically all these measurements.

RV has either been measured invasively or with an unacceptable reproducibility (ATSIERS, 1993). Commercially available infant pulmonary function equipment is not designed to measure RV. I have two separate infant systems that were used in unison to perform the measurement. RV measurements were very reproducible, mostly within 5%, and in five patients, 2%. In each infant, measurements of RV and FRC were reproducible and did not overlap even in the presence of a significant airway obstruction or tachypnea. I anticipate RV measurements will be routinely done in every infant pulmonary lab in the world. The measurements of RV, $TLC_{30}$ and FRC will provide the most comprehensive assessment of lung volumes in infants, in health and disease, from birth until three years. I think lung growth can be more reliably assessed by RV and $TLC_{30}$ than FRC alone. The ratio of $RV/TLC_{30}$ is important in studying air trapping in the lung, as is the case in older children and adults, in diseases such as bronchopulmonary dysplasia in infants born prematurely and cystic fibrosis.

$TLC_{30}$ has been measured invasively by tracer gas (Thorsteinsson et al., 1994) and nitrogen (Hammer et al., 1998) washout in intubated infants in the intensive care unit. We measured it noninvasively in three ways:

1. Raising the lung volume ($V_{30}$) to an airway opening pressure ($P_{ao}$) of 30 cm $H_2O$ then allowing expiration to proceed passively. The squeeze jacket for rapid thoracoabdominal compression (RTC) is triggered before the end of the passive expiration to induce a forced expiration down to residual volume (RV). Flow is integrated to produce volume, the vital capacity (from $V_{30}$ down to RV). By measuring the volume of nitrogen expired after end-forced expiratory switching of the inspired gas from room air to 100% oxygen while thoracoabdominal compression was maintained during the post-expiratory pause, RV is estimated. $TLC_{30}$ represents the sum of RV and the expired volume (vital capacity) from $V_{30}$ down to RV. By analyzing the airway pressure signal, the exact switching time is determined as well as a characteristic negative deflection caused by the outward springing of the compressed chest, occurring synchronously with jacket deflation.

2. By raising the lung volume to $P_{ao}$ of 30 cm $H_2O$, and measuring the volume of nitrogen expired after switching the infant at $V_{30}$ from room air into 100% oxygen, $TLC_{30}$ was estimated.

3. Measuring the forced vital capacity (FVC) from $V_{30}$. Then, measuring RV separately as described in paragraph 1 above. $TLC_{30}$ equals FVC plus RV (as described in the following detailed description).

After extensive in vitro experiments, using a calibrated syringe as a lung model, we found that the incorporation of a collapsible breathing bag in the nitrogen washout circuit enhanced the reproducibility in vivo and the accuracy in vitro of measured washout volumes.

The technique may be used for routine clinical as well as research studies of lung function in infants from birth until three years of age. It will assist in defining the normal development and growth of the lungs, to determine the efficacy of therapeutic interventions (surfactant treatment in premature newborns, liquid ventilation in critically ill infants, and the use of pulmozyme in cystic fibrosis), and to evaluate the relation between lung injury in early life and chronic lung disease. It has the potential of being similarly used in experimental animal studies as well.

An automated system can be designed and programmed to perform the measurements. Using a three-way balloon valve, such a system would be capable of automatically raising the lung volume to $V_{30}$, triggering the squeeze jacket, and switching the patient into $O_2$. The maneuvers can be summarized as follows:

1. Measurement of FVC: Hyperventilate the infant; raise to $P_{ao}$ of 30 cm $H_2O$; hold for 0.06 s; trigger the jacket; deflate the jacket after 3 (or 4) seconds.

2. Measurement of RV: Hyperventilate the infant; trigger the jacket before the end of the last passive expiration; switch the infant into $O_2$ (to measure the volume of expired nitrogen) before the decline of the jacket pressure plateau and when the airflow and $P_{ao}$ are zero; deflate the jacket.

3. $TLC_{30}=1+2$.

4. Measurement of $TLC_{30}$ alone: Hyperventilate the infant; raise to $P_{ao}$ of 30 cm $H_2O$, hold, switch the infant into $O_2$ to measure the volume of expired nitrogen.

5. An automated system can be made to measure FVC and RV in the same breath.

BRIEF DESCRIPTION OF THE DRAWINGS

FIG. 1 is a schematic view of the nitrogen washout circuit. FIGS. 1A and B schematically illustrate operation of the apparatus when the infant is breathing air (FIG. 1A) and oxygen (FIG. 1B), respectively.

FIGS. 3A, 3B, 3C and 3D are four graphs showing the measurement of the residual volume (RV) with example traces of flow, volume, airway opening pressure ($P_{ao}$) and jacket pressure ($P_j$) from infant #6.

FIGS. 4A–4D, 5A–5D, and 6A–6D are graphs illustrating the measurement of the residual volume in patients (pt) 2, 7, and 6, respectively, zoomed on the time period that begins with jacket inflation and ends at the $20^{th}$ second of the data collection period. Each of FIGS. 4A–4D, 5A–5D and 6A–6D, respectively, includes a trace of flow, volume, airway opening pressure ($P_{ao}$), and jacket pressure ($P_j$).

FIGS. 7A and 7B show the measurement of the residual volume including traces of $P_{ao}$ and $P_j$, respectively, from pt 3. It zooms on the period between the switching into oxygen and ends at the $20^{th}$ second.

DETAILED DESCRIPTION OF THE PREFERRED EMBODIMENTS

Figures 2A, 2B, 2C:
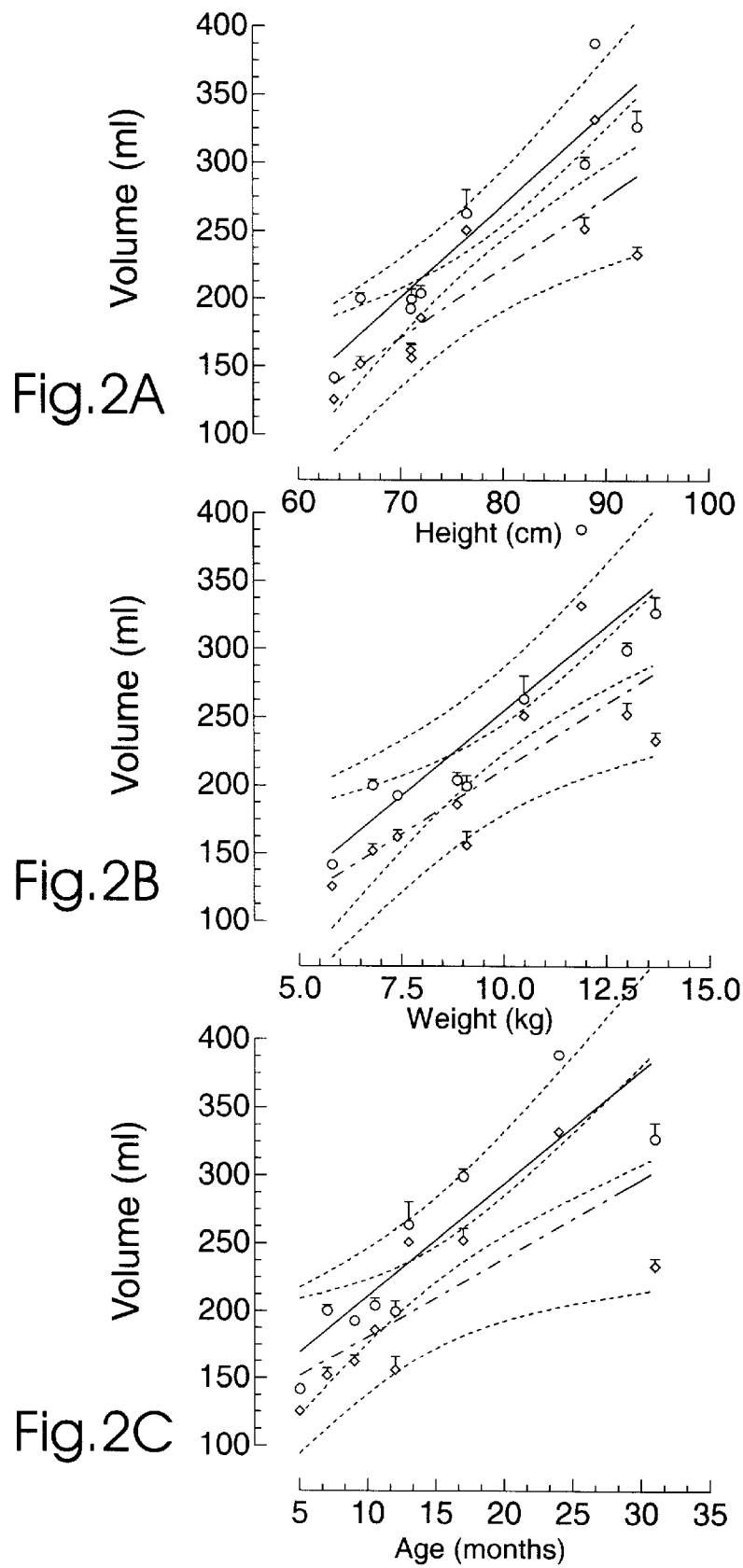
FIGS. 2A, B, C are graphs of the mean (SD [T]) of residual volume (RV) [◇] and functional residual capacity (FRC) [o] from each infant plotted against the respective height, weight and age. The straight dashed and solid lines are RV and FRC regression lines, respectively. The curved dotted lines represent the 95% confidence limit.
Figures 5A, 5B, 5C, 5D:
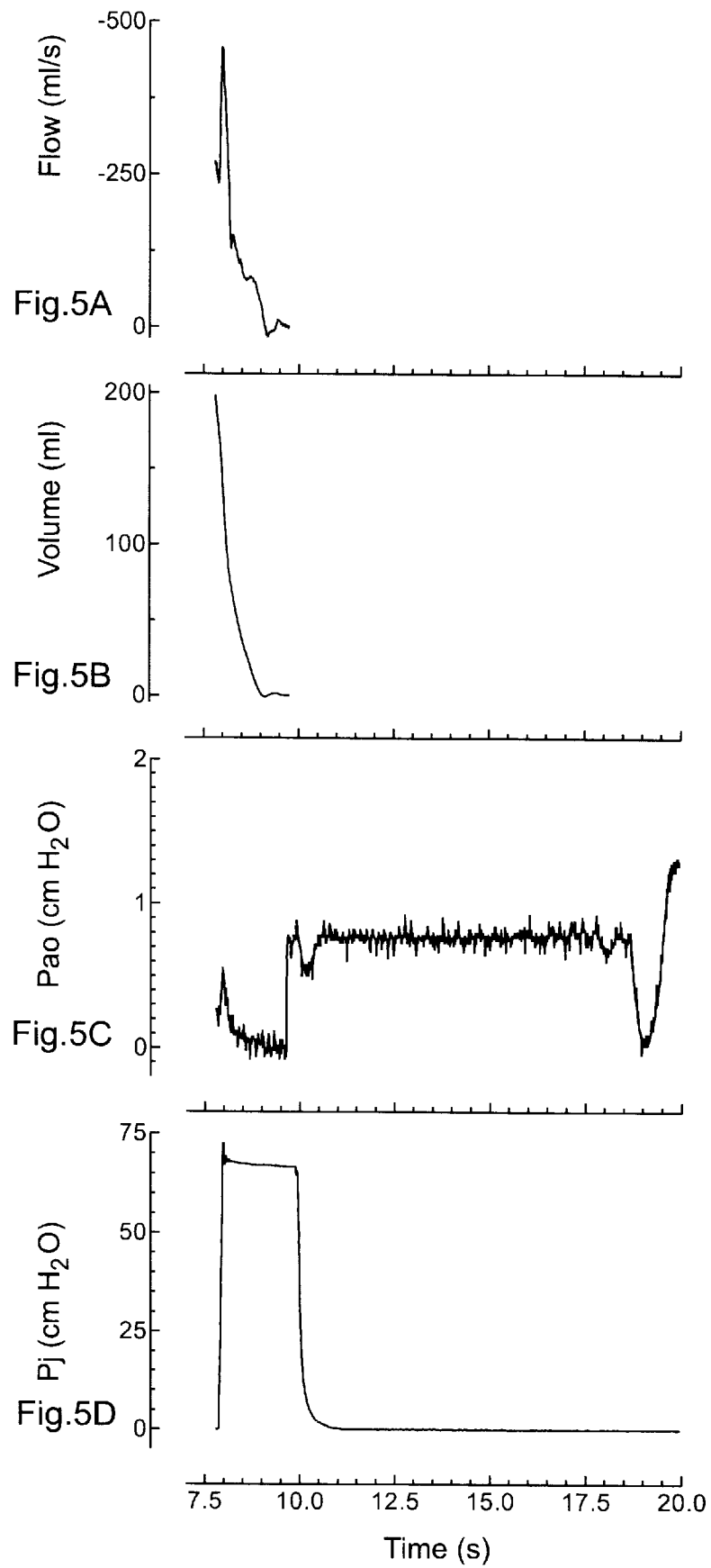
Figures 6A, 6B, 6C, 6D:
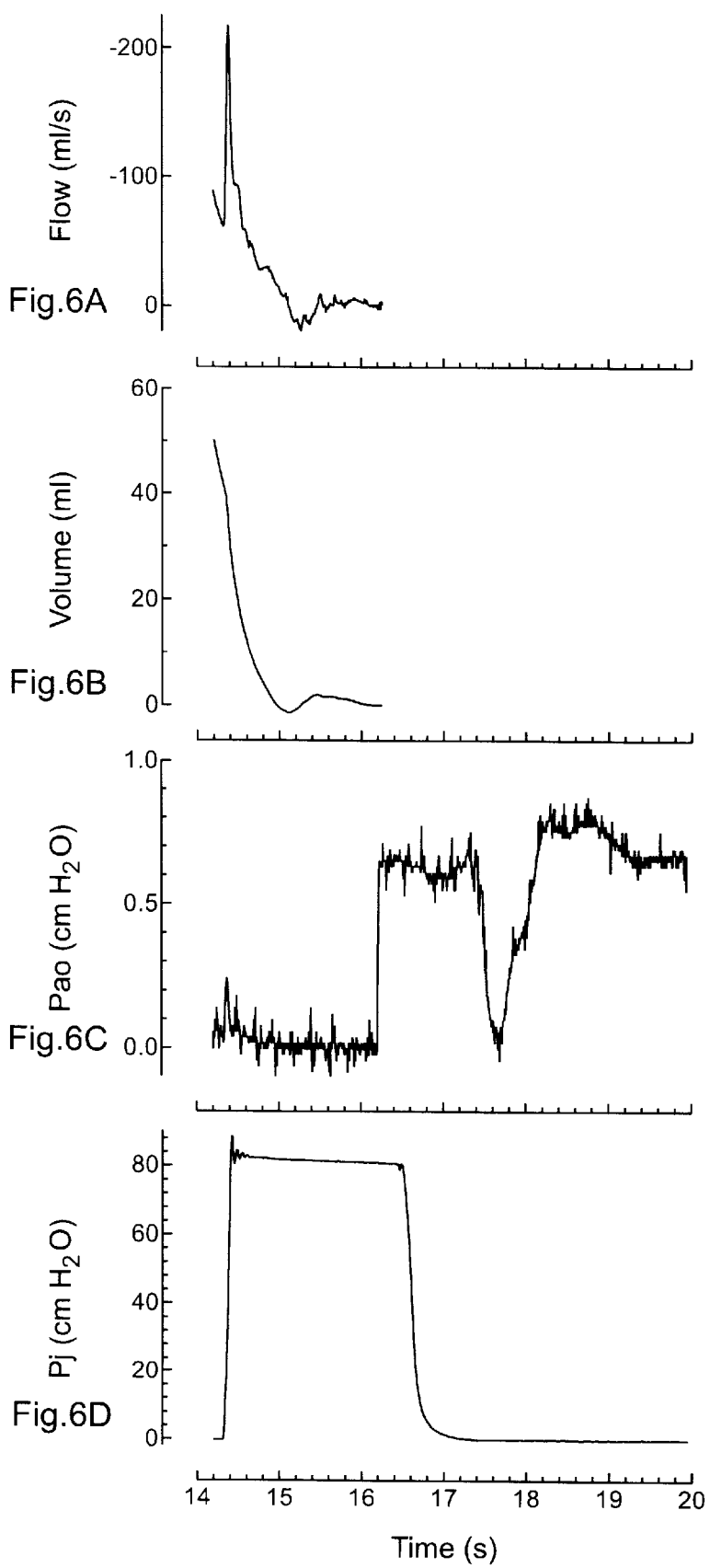

The functional residual capacity (FRC), the only lung volume to be routinely measured in infants, is an unreliable volume landmark. Besides FRC, we measured the residual volume (RV) by $N_2$ washout using rapid thoracoabdominal compression (RTC) in nine infants (age range, 5–31 mo) with cystic fibrosis, sedated with po chloral hydrate (80–100 mg/kg)+/−hydroxyzine (0.25–0.5 mg/kg). We used a commercial system (SensorMedics, CA) for $N_2$ washout and a custom-made system to perform RTC. RTC was performed from a raised lung volume ($V_{30}$) to an airway opening pressure of 30 cm $H_2O$. The jacket pressure ($P_j$) (range 65–92 cm $H_2O$) which generated the highest forced expiratory volume {range, 23.3–49.1 ml/kg; (mean) 40.2 ml/kg; 95% confidence interval [C1] 33.03, 47.33}, was used during the RV maneuver. The infant was manually hyperventilated to briefly inhibit the respiratory drive. RTC was initiated during the last passive expiration. By measuring the volume of nitrogen expired after end-forced expiratory switching of the inspired gas from room air to 100% oxygen while RTC was maintained during the post-expiratory pause, RV was estimated. The mean (SD) period between the switching to $O_2$ and the end of the $P_j$ plateau was 0/301 (0.187) s. The duration of the $N_2$ washout was longer for RV than for FRC: 80.9 (17.9) vs 72.4 (14.0) s (p<0.001). In each infant, RV and FRC measurements were reproducible and did not overlap; the difference (expiratory reserve volume) between means was statistically significant (p<0.05). Mean RV was 21.3 (CI 18.7,24.0), RFC, 25.5 (CI 22.8, 28.1) and $TLC_{30}$ (total lung capacity at $V_{30}$), 61.5 (CI 54.4, 68.7) ml/kg. Means exhibited body length and weight as well as age dependence. When measuring RV, the period between the switching to $O_2$ and the end of the $P_j$ plateau was 0.301 (CI 0.211, 0.391) s. The RV washout duration was longer than FRC's: 80.9 (CI 71.3, 90.4) was 72.4 (CI 64.9, 79.8) s (p<0.001). We have developed a new, noninvasive and reliable technique for routine measurement of RV in infants.

The preferred embodiments of the present invention are described with respect to FIGS. 1, 1A, and 1B which schematically illustrate the nitrogen washout circuit. The infant is fitted with face mask 30 and breathes through the three-way slide valve 14, pneumotachometer 21 and Y-adapter 20. Air is introduced through inspiratory limb 25 of Y-adapter 20 and expired through expiratory limb 22 of Y-adapter 20 when three-way slide valve 14 is operated for air breathing (shown schematically in FIG. 1A). The long parallel dotted lines 10 point to the connection site of the central port 12 of the aerosol 'T' adapter 13 onto the inlet-outlet port 11 of the slide valve 14. Oxygen is introduced through inlet 31 of aerosol "T" adapter 13 and when slide valve 14 is operated so as to allow the infant to breath oxygen, the oxygen-nitrogen washout is expired from outlet 32 of aerosol "T" adapter 13. A breathing bag 40 may be inserted into the circuit by means of "T" connector 41 to inlet 31 of aerosol "T" adapter 13.

When measuring the residual volume (RV), the Y-adapter 20 is connected to the pneumotachometer (vertical, parallel fine-dotted lines) 21. Occlusion of the expiratory limb 22 of the Y-adapter 20 diverts the air to the infant, raising the lung volume to an airway opening pressure plateau set at 30 cm $H_2O$ by the pressure relief valve 23. Side views of the circuit depict the path (arrows inter-connected by a dotted line) of air (FIG. 1A) and, after activating the slide valve 14, of oxygen (FIG. 1B) in and out of the of the infant's airway. Note that after the slide valve 14 switches the infant into $O_2$, he no longer breathes through the pneumotachometer 21. When breathing air, the flow through the pneumotachometer 21 is measured by the flow transducer 24. Integration of the flow produces the volume.

Subjects and Methods

Subjects

Nine Caucasian infants and young children (five boys, four girls) with a median age of 12 months (range, 5 to 31 months) who have CF and regularly attended the outpatient clinic of Arkansas Children's Hospital were tested during their routine infant lung function testing. Patients were excluded from testing if they were clinically unstable, had a significant upper airway obstruction, or a recent thoracic or abdominal surgical procedure. The median weight was 9.1 kg (range, 5.8 to 13.7), and median length was 72.0 cm (63.5 to 93.5). Patients' characteristics are presented in Table 1 following:

TABLE 1

Subjects' data and percent predicted volume results

| Subject # | Sex | Age mos | Weight Kg | Height cm | EDS[+] ml | FRC % Pred | TLC$_{30}$ % Pred† | Pj cm H$_2$O |
|---|---|---|---|---|---|---|---|---|
| 1 | M | 9 | 7.4 | 71.0 | 12 | 110 | 102 | 83¤ |
| 2 | M | 24 | 11.9 | 89.0 | 12 | 125 | 101 | 93 |
| 3 | M | 5 | 5.8 | 63.5 | 14 | 108 | 107 | 65 |
| 4 | F | 31 | 13.7 | 93.1 | 10 | 94 | 96 | 85¤ |
| 5 | F | 13 | 10.5 | 76.5 | 13 | 125 | 79 | 75¤ |
| 6 | M | 7 | 6.8 | 66.1 | 15 | 138 | 86 | 79¤ |
| 7 | F | 10.5 | 8.9 | 72.0 | 15 | 113 | 83 | 70 |
| 8 | M | 17 | 13.0 | 88.0 | 8 | 100 | 76 | 79 |
| 9 | F | 12 | 9.1 | 71.1 | 12 | 114 | 80 | 70 |

M, male;
F, female;
EDS, effective dead space of the face mask;
FRC, functional residual capacity;
Pred, predicted;
TLC$_{30}$, total lung capac*ity at a raised lung volume to a Pao of 30 cm H$_2$O and represents the sum of FVC and RV from each subject;
Pj, jacket pressure. FRC and RV were corrected for EDS and converted to BTPS.
[+]EDS was measured in each infant with a water volumeter
Prediction equation from collated data
\Prediction equation from Thorsteinsson et al
*This Pj generated the highest FVC and was used when measuring residual volume (RV) by N$_2$ washout
¤A Pj higher by 10 cm H$_2$O was used once when measuring RV and did not result in a lower RV Feeds were withheld and sleep deprivation was encouraged for three hours before the patient was to be sedated. Parents were instructed to feed their baby just prior to this 3-hour period. Patients were sedated with 80–100 mg/kg p.o. chloral hydrate. A maximum dose of one gram was not exceeded. One toddler did not sleep within 20 min. after the maximum drug dose had been administered, and another had a history of not becoming sedated with chloral hydrate; they received, in addition, p.o. hydroxyzine (Nathan J E and West S M. Comparison of Chloral hydrate-hydroxyzine with and without meperidine for management of the difficult pediatric patient. *J Dent Child* 1987; 437–44.), 0.25 and 0.5 mg/kg, respectively. After the full sedative dose was administered, a hungry infant was allowed to suck a few times on a bottle containing apple juice. The Infant Pulmonary Function Laboratory sedation policy and precautions were adopted. Patients were continuously monitored during the entire study with a Pulse Oximeter (Nellcor Inc., Pleasenton, Calif.). The ethics committee of the institution approved the testing protocol. An informed written parental consent was obtained for each infant prior to testing and parents were present during tests.

Testing Protocol

Once asleep, the infant was placed supine on the testing table with the head tilted back gently into a "sniffing"

(neutral) position. RVRTC maneuvers were performed from $V_{30}$, i.e., a raised lung volume to a predetermined airway pressure ($P_{ao}$) of 30 cm $H_2O$. Increasing jacket pressures ($P_j$) were used until the largest FVC, defined as the forced expiratory volume between $V_{30}$ and RV, was obtained as indicated by a decline or a plateau in FVC with a further increase in $P_j$. The $P_j$ that generated the highest FVC was used during the RV measurement. Additionally, in four subjects, a $P_j$ higher by 10 cm $H_2O$ was used once to find out whether further chest compression could have generated a smaller RV. RV and FRC measurements were performed at random. A period of at least twice the washout time was allowed between measurements.

Before the chloral hydrate was given, weight measurement was performed with a balance (Detecto, Webb City, Mo.) that was checked for accuracy before each patient test. Weight was rounded to the nearest 20 gm. Two trained adults performed the stature measurement after the lung function test had been completed. We used a custom-made stadiometer which had two 91.5 cm long steel rulers (Macklanburg-Duncan, Oklahoma City, Okla.). They were mounted on the bottom and sideboards, exactly 20 cm from the headboard. Repeat measurements within 0.5 cm of each other were obtained. Measurements of length were made to the nearest millimeter (Stocks J, Quanjer PhH. Reference values for residual volume, functional residual capacity and total lung capacity. *Eur Respir J* 1995; 8, 492–506.).

Methods

Equipment

A commercial system, the Pediatric Pulmonary Unit (PPU) 2600 (SensorMedics, Anaheim, Calif.) was used to measure RV and FRC by $N_2$ washout. A custom-made computer-controlled system (CCCS) was used to perform RVRTC. It was also used to adapt the PPU for measuring FRC and RV. First, to introduce the pneumotachometer into the circuit while the infant was breathing room air in order to compensate for switching-errors above end-tidal expiration when FRC was measured (Gappa M, Fletcher ME, Dezateux Calif., et al. Comparison of nitrogen washout and plethysmographic measurements of lung volume in healthy infants. Am Rev Respir Dis 1993; 148, 1496–1501.). Second, to display signals-flow (F), $P_{ao}$, $P_j$ and flow-volume loops-in real-time on a 21-inch computer monitor screen to enable the operator to perform sequential activations of the jacket inflation and slide valve in a timely fashion during RV measurement. Third, to perform RTC for RV measurement.

CCCS for RVRTC: The system was previously described (Hayden M J, Sly P D, Devadason S G, et al. Influence of driving pressure on raised-volume forced expiration in infants. *Am J Respir Crit Care Med* 1997; 156, 1876–83.). The compression jacket consisted of an inflatable plastic plate held over the chest and abdomen with a firm vinyl outer layer (VOL). RTC was performed with the arms outside the jacket to avoid possible splinting of the chest wall (Steinbrugger B, Alnigan A, Raven J M, et al. Influence of the "squeeze jacket on lung function in young infants". *Amer Rev Respir Dis* 1988; 138, 1258–60.). The VOL ('Herculite 80', Vicar International, New Jersey, N.J.) was modified for the present study by inserting a 14 in. zipper ('separating Sport zipper'; Coats and Clark, Greenville, S.C.) so that the VOL could be loosened during FRC measurement, with minimal disturbance to the sleeping infant, to avoid any possible limitation to chest wall excursions during tidal breathing. Tensile resistance was maximized by covering the zipper with a strip of the firm vinyl on each side of the zipper teeth. With the zipper sandwiched between the vinyl strips and VOL, it was further anchored to the VOL by stitching through the strips, zipper and VOL. Furthermore, the zipper extended 5 cm beyond the upper and lower edges of the VOL to ensure that a uniform tension extended to the very edge of the VOL. In pilot studies, a $P_j$ plateau was attained in <0.1 sec and comparable flow-volume curves were obtained using VOL with and without a zipper in the same subject (M. G. Morris, personal observations). The inflatable plastic plate was connected to a large plastic reservoir (15 gal. 'Tight Head Drum'; Basco Co.; University Park, Ill.) via a series of large-bore (>2.5 cm) solenoid valves and tubing.

A soft plastic air cushion mask 30 (Kings Systems, Noblesville, Ind.) was held on the mouth and nose forming an airtight seal. The mask connection port had a 10 mm inner diameter (ID) that was cut out and replaced with a 22 mm ID connection. Airway opening pressure ($P_{ao}$) was measured with a pressure transducer 31 (FPM-02PG; Fujikura, Tokyo, Japan) from a port mounted into the dome of mask 30. One end of a heated 0–160 L/min screen pneumotachometer 21 (PNT) (Hans Rudolph Inc., Kansas City, Mo.) was connected to the mask port; the other, to a one-way balloon-valve (Model 9340; Hans Rudolph Inc.). The latter, in turn, was connected to a series of solenoid valves that allowed for inflation of the infant's lungs to a predetermined $P_{ao}$ of 30 cm $H_2O$ ($V_{30}$) by means of a fan pump (Inflate-all; Coleman Co. Inc., Wichita, Kans.). The inflatable jacket was then pressurized and forced expiration proceeded from $V_{30}$ to RV. The sequence of valves was controlled by BRATLAB software (RHT-INFODAT, Montreal, PQ, Canada) on a computer. This integrated software sensed $P_{ao}$, halted inflation, and initiated expiration. The differential pressure across the PNT was measured with a 0 to 7 cm $H_2O$ differential pressure transducer (PX170-07DV; Omega International Corp., Stamford, Conn.) and amplified (SC14C; RHT-INFODAT, Montreal, Canada) in order to measure flow. Flow was integrated to produce volume. All signals were collected and analyzed on computer with LABDAT-ANADAT 5.2 data acquisition and analysis software (RHT-INFODAT).

As shown in FIG. 1, a Y-adapter 20 with a central mount (Bird Products Corporation, Palm Springs, Calif.) was used to hyperventilate the infant with several rapid inflations prior to RVRTC. It was transformed into a 4-way (limbs) connection by rupturing the base inside the central mount. One limb (22 mm ID) was connected to the distal end of the one-way balloon-valve. A calibrated pressure relief valve 23 (Newport Medical Instruments Inc., Newport Beach, Calif.) that limited maximal pressure to 30 cm $H_2O$, was embedded in the second limb (22 mm ID). The third limb 25 (15 mm ID) was connected to a constant airflow of 15 L/min. Occlusion of the fourth (expiratory) limb 22 (17 mm ID) diverted the airflow to the infant via the balloon valve and PNT causing lung inflation. Prior to RVRTC, several rapid inflations were delivered to the infant lungs by occluding the expiratory limb 22 of the Y-adapter 20 until the infant's respiratory drive was inhibited. Then, the fan-pump was activated to deliver the last inflation to the infant via the PNT and face-mask to a predetermined $P_{ao}$ of 30 cm $H_2O$, then the airway was occluded for 0.05 s by inflating the balloon and the jacket was rapidly inflated while the airway remained closed. A second plateau in $P_{ao}$ occurred. Once the airway was opened, forced expiration proceeded from $V_{30}$ to RV. Jacket pressures were started at 50 cm $H_2O$ and increased by 10 cm $H_2O$ until no further increase in FVC was observed. $P_j$ was measured with a pressure transducer (FPM-02PG). The $P_j$ that generated the highest FVC was used during the RV maneuver (see below). At least two highest FVC measurements within 5% were obtained.

Calibration of the PNT was performed with a high precision calibrating flowmeter that had high-resolution valves (Gilmont Instruments, Barrington, Ill.). Calibration was re-checked by injecting and withdrawing known air volumes (100, 200, 300 and 500 ml) from a calibrating syringe and integrating the flow signal to produce volume. The latter differed by less than 0.5% from the known volume. The mouth's pressure transducer was calibrated with a U-shaped water manometer (range 0–60 cm $H_2O$; Dwyer Instruments Inc., Michigan City, Ind.) and the jacket's, with a diaphragm-operated differential pressure manometer. ('Magnehelic', range 0–150 cm $H_2O$; Dwyer Instruments Inc.).

The Nitrogen Washout Technique:

The open circuit $N_2$ washout method for assessment of $FRC_{N2}$ as described by Gerhardt et al (Gerhardt T, Hehre D, Bancalari E, et al. A simple method for measuring functional residual capacity by $N_2$ washout in animals and newborn infants. *Pediatr Res* 1986; 20, 668–71.) entails measuring the volume of nitrogen expired after end-tida/ expiratory switching of the inspired gas from room air to 100% oxygen. In the present study, $RV_{N2}$ was also estimated after end-forced expiratory switching. At a constant bias flow that exceeds the infant's inspiratory peak flow during tidal breathing, the integrated expired $N_2$ is multiplied by the constant flow of $O_2$ to obtain the volume of expired $N_2$. A two-point calibration is performed with known air volumes. With the amount of $N_2$ washed out measured and the initial fractional alveolar $N_2$ concentration is known ($F_{Ai,N2}$: room air=0.79), then the lung volume at which the washout was initiated can be calculated (Tepper R S, Merth I T, Newth C J L, et al. Measurement of functional residual capacity in infants by helium dilution and nitrogen washout techniques. In: J Stocks, P D Sly, R S Tepper, W J Morgan (eds): Infant Respiratory Function Testing. New York: John Wiley & Sons, Inc, 1996: 165–89.):

Lung volume (FRC or RV)=Volume $N_2$ washed out$\div F_{Ai,N2}$

The PPU has an operator-controlled pneumatic slide valve that switches the infant to breathing 100% $O_2$. Then, the expired gas enters a mixing chamber that is connected via a precision needle valve and a vacuum pump to a $N_2$ analyzer, and the $N_2$ concentration is integrated electronically by the PPU signal processing system. The $N_2$ washout curve is displayed in real-time on the computer monitor. When a 0% $N_2$ concentration is displayed on the monitor, the slide valve is activated and the infant is switched back to breathing room air, and $FRC_{N2}$ or $RV_{N2}$ are automatically calculated by the system. In the present study, the latent period before the rise above baseline of the $N_2$ washout curve as well as the washout duration were recorded.

Volume was corrected for the effective dead space of the face-mask and the slide valve port (Morris M G. Measuring the effective dead space of face mask in infants. *Am J Respir Crit Care Med* 1999; (Abstr.) (submitted for publication).) and converted to BTPS. Ambient room temperature and relative humidity were measured with a certified Hygrometer and Temperature Indicator (Abbeon Cal.Inc., Santa Barbara, Calif.). Daily Barometric Pressure readings were obtained from a mercury manometer (Princo, Southampton, Calif.).

In pilot studies, we overcame these difficulties: A change in $N_2$ calibration over time that was also previously reported, measuring the effective dead space for each infant by using a newly developed volumetric technique, and switching the slide valve at end-forced expiration to measure RV. We also desired to establish the linearity of the system over a wide range of volumes so that a single two-point calibration could be employed to measure RV and FRC. Our overall aim was to increase the precision and accuracy of measurements so that small differences between RV and FRC could be detected. The methodology which yielded the best results, was the following:

The nitrogen washout circuit (FIG. 1). A three-way pneumatic slide valve (8540 Series-9.5 mm Flow Bore Size; Hans Rudolph Inc.) was used. It had a mouth Port (22 mm outer diameter (OD)×15 mm ID), and two other smaller inlet/outlet ports (15 OD×10.5 ID mm). The oxygen flow of a high precision flowmeter (Timemeter Instrument Corporation, Lancaster, Pa.) was accurately set by adjusting the middle of the float to the 10 L/min mark. This flow rate was used for all tests. The $O_2$ tubing (King Systems Corporation, Noblesville, Ind.) was connected to the ⅛ in. ID end of an adapter (Hospitak Inc., Farmingdale, N.Y.) whose other end (22 mm ID) fitted on the 22 mm OD of a 'T' connection ('T' piece; Intersurgical Inc., Cazenovia, N.Y.). A 0.5 L collapsible breathing bag (Vital Signs Inc., Totowa, N.J.) was attached to the center port (22 mm ID) of the 'T' connection via an adapter (22 mm OD/19 mm ID×22 OD/17 ID mm) (Baxter Healthcare Corporation, Deerfield, Ill.). The distal (third) end (22 mm ID) of the 'T' connection was fitted onto an aerosol 'T' adapter (22 mm OD) (Hudson Respiratory Care Inc., Temecula, Calif.). The center port (15 mm ID) of the aerosol 'T' adapter was inserted onto the small port (15 mm OD) of the 3-way slide valve situated at a right angle from the mouth port. The opposite end (22 mm OD) of the aerosol 'T' adapter was inserted in a distensible coupling connector (29 mm OD×17 mm ID) (Marquest Medical, Aurora, Colo.) and a very snug fit was obtained. A 'Concha Hose Adapter' (Respiratory Care Inc., Arlington Heights, Ill.) joined with a snug fit the other end of the coupling connector and the proximal end of a 2.0 m long hose ('Tygon' ⅜ in ID×⅝ in OD; Baxter Healthcare Corporation). The distal end of the hose was inserted onto the 11 mm OD end of an adapter (Marquest Medical, Aurora, Colo.) whose other end (22 mm ID) fitted snugly on the inlet port of the nitrogen mixing chamber. On this chamber's outlet port, a 1.8 m long (22 mm ID) corrugated tube (Baxter Healthcare Corporation) was attached and was loosely coiled in an open box on the side of the PPU. This tube prevented ambient air from diffusing back in the nitrogen mixing chamber.

Calibration of the PPU. As recommended by the manufacturer, using separate electrical outlets, the vacuum pump with its $O_2$ flow was turned on 30 min, the PPU measurement module and computer, at least 20 min before calibrating. The breathing bag was squeezed manually several times to wash out any $N_2$. The computer software $N_2$ Calibration Menu was accessed. The displayed nitrogen concentration was 0.0%; if not, it was zeroed using the 'autozero' mode of the PPU software. A check for the presence of a baseline drift was then performed. The menu of the 'Low' (or 'High') volume calibration was accessed. When the displayed $N_2$ concentration was 0.0%, the slide valve was activated and the mouth port was left open to room air for 10 sec in order to wash out the air within the port by the pure $O_2$. The port was then occluded to prevent room air from diffusing back into the port. The $N_2$ concentration and the integrated % nitrogen signal (INS) were observed for 90 sec for a stable 0.0 reading. If the INS were to rise, then a baseline drift was presumed to be present, the 'Escape' key on the computer keyboard was pressed and the calibration menu was re-accessed. Though the displayed $N_2$ concentration was still 0.0%, a further decrease of the baseline towards zero was performed using 1–3 keyboard strokes in the 'manual' mode of the program, followed by a repeat check for a baseline drift. Over-correction, which resulted in a negative % $N_2$ concentration reading, was not allowed. Additional checks for baseline drifts—and correction if needed—were undertaken during the waiting periods between measurements on a patient, with the slide valve being activated via the 'Patient test' menu, as opposed to the 'Calibration' menu used initially.

Calibration of the nitrogen analyzer needle valve was performed before each patient test. The needle was removed from the mixing chamber outlet port and allowed to hang for at least 45 min so that room air was sampled. The procedure of "peaking the needle", as described by the manufacturer, was performed to obtain the optimum negative pressure in the analyzer to achieve maximum nitrogen ionization. When the needle was replaced into the outlet port, the displayed $N_2$ concentration was 0.0%. The low and high volume calibration was performed with 42 and 342 ml of air, respectively, for all patient tests. When the INS stopped rising, it was recorded, the 'Escape' key was pressed and each volume calibration was repeated until two successive INS within 1% were obtained before the calibration was entered. Accuracy of the calibration was re-checked immediately after calibrating by measuring known volumes of air (see below). It was also re-checked after patient testing had been completed using a sterilized $N_2$ circuit (slide valve, connectors and a new collapsible breathing bag) to prevent contamination of the calibrating syringe. A known volume equivalent to the patient's measured lung volume was included in re-checking the calibration. Finally, the nitrogen analyzer needle was removed from the $N_2$ mixing chamber's outlet port and allowed to hang for about 15 min for room air to be sampled. The displayed $N_2$ concentration was 79.0±0.2 after all patient tests.

Measurement of the Functional Residual Capacity:

The PPU was adapted by connecting the PNT-attached to its flow transducer—of the CCCS to the 22 mm ID end of a plastic adapter (Baxter Healthcare Corporation) whose other 15 mm ID end fitted on the second small port of the 3-way slide valve (FIG. 1). Prior to FRC measurement, the VOL was unzipped to avoid any splinting of the chest during tidal breathing. The slide valve's mouth port was connected to a size 1 transparent face mask (Rendell-Baker Soucek Pediatric Face-mask; Gary Hull Anesthesia, Huntington Beach, Calif.) which was held onto the infant's face with silicone putty ('Theraputty', North Coast Medical Inc., San Jose, Calif.) and an airtight seal was achieved. While the infant was breathing room air, flow-volume loops were displayed in real-time on the computer monitor of the CCCS. After observing a stable tidal breathing, the slide valve was activated close to end-expiration as possible. After the $N_2$ washout had been completed, the slide valve was activated and the infant was switched back to breathing room air. Each INS and the corresponding calculated volume were recorded. The slide valve assembly was removed from the infant's face in between measurements. Flow was integrated to produce volume. FRC measurement was corrected for any volume above exact end-tidal expiration when switching the slide valve. At least two FRC measurements within 10% were obtained.

Measurement of the Residual Volume:

The Y-adapter -described above- was connected to the PNT-slide valve assembly to perform rapid lung inflations (FIG. 1). Airway opening pressure ($P_{ao}$) was measured with a pressure transducer (FPM-02PG) from a port mounted into the dome of the clear mask. Signals (F, $P_{ao}$ and $P_j$) displayed in real-time on the CCCS computer monitor screen, were collected and analyzed on computer with LABDAT-ANADAT 5.2 data acquisition and analysis software (RHT-INFODAT).

The slide valve assembly was connected to the clear face mask which was kept on the infant's face with an airtight seal by means of the silicone putty. The RV measurement was performed by one operator. The PPU and CCCS computers' keyboards were brought close to the sleeping infant by means of extension cables. Several rapid inflations were delivered to the infant lungs by occluding the expiratory limb of the Y-connection until the infant's respiratory drive was inhibited (FIG. 1A). After the last inflation, the flow limb of the flow-volume loop signal was watched closely on the monitor screen. Expiration was allowed to proceed initially passively, then jacket inflation was activated during the last portion of exhalation to induce a forced expiration. Once jacket inflation was triggered, the $P_j$ signal was instantaneously observed. The slide valve was activated, switching the infant to breathing 100% $O_2$ (FIG. 1B) before the decline of the $P_j$ plateau which coincided with maximum chest compression (FIGS. 3A–3D). The total duration of jacket inflation was set for three seconds. When a 0% $N_2$ concentration was displayed on the PPU monitor, the slide valve was activated and the infant was switched back to breathing room air. Three criteria were set for an acceptable RV measurement. When the slide valve was switched, the air flow (F) and pressure ($P_{ao}$) at the mouth had been zero while a maximal chest compression was maintained as indicated by a raised $P_j$ plateau. The period between the activation of the slide valve and the end of the $P_j$ plateau was estimated for each RV measurement (see Results below). At least two RV measurements within 10% were obtained.

Accuracy Study with a Lung Model:

When our 0.5 L calibrating syringe (Hans Rudolph Inc., Kansas City, Mo.), with its piston pushed in to the 500 ml mark, was connected to the slide-valve mouth port (22 mm OD×15 ID), their combined volume was found to be 42 ml. This was estimated by volume replacement and was further confirmed by Hans Rudolph Inc. This volume was not subtracted during calibration. The gas space within the slide-valve piston body was ignored because it was flushed with oxygen during testing for baseline drifts. Following a two-point calibration, we used the syringe as a lung model to washout known air volumes from 42 to 492 ml. The background flow of $O_2$ was set at 10 L/min. Each measurement was repeated five times. Using roughly 50–75 ml stroke volumes, different known air volumes were randomly used over a fourteen-hour period to find out if changes in calibration occurred over time.

Introduction of the collapsible breathing bag into the $O_2$ circuit enhanced the reproducibility and precision of volume measurements. Therefore, using ~70 ml stroke volumes simulating tidal breathing, we studied the influence of the BB by comparing the flow and volume signals waveform before and after we introduced the BB into the circuit. This in vitro experiment was performed by inserting the PNT into the distal end of the corrugated tube whose proximal end was connected to the $N_2$ mixing chamber's outlet port.

Statistical Analysis:

Data were expressed as arithmetic mean and 95% confidence interval (CI). In figures, error bars represented the standard deviation (SD). Statistical analyses included Student's t test of unpaired and paired data. Mean RV and FRC measurements from each patient were compared using the unpaired t-test. A mean value for the total lung capacity at $V_{30}$ ($TLC_{30}$) was derived from the sum of mean RV and FVC for each patient. Means from all patients were regressed against their respective age, height and weight measurements. The regression line and the 95% confidence limits were graphed. The slope and intercept of regression equations for RV, FRC, FVC and $TLC_{30}$ were presented as mean and standard error (SE) and compared using the unpaired t test (Zar JH. Biostatistical analysis. 3rd ed. New Jersey: Prentice Hall, 1996: 317–70.). The coefficient of determination ($r^2$) was also computed. Individual FRC (FRC) [o] from each infant plotted against the respective height, weight and age. The straight dashed and solid lines are RV and FRC regression lines, respectively. The curved dotted lines represent the 95% confidence limit.

In the linear regression analysis, means of RV and FRC exhibited body length and weight as well as age dependence (FIG. 2; Table 2).

TABLE 2

Lung volumes versus height, weight and age

|  | Slope | RV Y-intercept | $r^2$ | Slope | FRC Y-Intercept | $r^2$ |
|---|---|---|---|---|---|---|
| Height | 5.2 (1) | −191.4 (98) | 0.704 | 6.8 (1) | −278.6 (78)* | 0.868 |
| Weight | 19.1 (5) | 20.6 (53) | 0.651 | 24.9 (5) | 5.4 (50)* | 0.777 |
| Age | 5.8 (2) | 122.7 (33) | 0.548 | 8.3 (2) | 128.3 (27) | 0.782 |

|  | Slope | FVC Y-intercept | $r^2$ | Slope | $TLC_{30}$ Y-Intercept | $r^2$ |
|---|---|---|---|---|---|---|
| Height | 18.0 (2) | −974 (159) | 0.916 | 23.2 (2)$^\phi$ | −1165 (116)$^\$$ | 0.972 |
| Weight | 66.6 (11) | −238.2 (107) | 0.849 | 85 (11)$^\phi$ | −217 (108)$^\$$ | 0.900 |
| Age | 23.6 (2) | 69.1 (24) | 0.973 | 29.4 (2)# | 191.8 (33) | 0.967 |

$r^2$, coefficient of determination;
RV, residual volume;
FRC, functional residual capacity;
FVC, forced vital capacity from $V_{30}$;
$TLC_{30}$, total lung capacity at a raised lung volume ($V_{30}$) to a Pao of 30 cm $H_2O$.
Mean (standard error)
All regression lines' slopes were significantly non-zero (p < 0.05)
The differences between corresponding slopes of RV and FRC were statistically insignificant (p > 0.3)
*Significantly different from corresponding intercepts of RV (p < 0.05)
$^\$$Difference extremely significant from FVC Y-intercept (p < 0.0001)
Significantly different from FVC (p < 0.05)
$^\phi$Difference insignificant from FVC: height, p = 0.06; weight, p = 0.23 results were expressed as percent predicted based on an equation from measurements of FRC by helium dilution from collated data from three separate studies:

$$FRC(ml) = 0.0036 * L^{2.531}$$

$TLC_{30}$ was expressed as per cent predicted based on an equation derived from a study on 40 children without lung disease in whom $TLC_{30}$ represented the sum of FRC, measured by tracer gas washout, and the inspiratory capacity at a Pao of 30 cm $H_2O$ (Thorsteinsson A, Larsson A, Jonmarker C, et al. Pressure-volume relations of the respiratory system in healthy children. *Am J Respir Crit Care Med* 1994; 150, 421–30.):

$$TLC_{30} = -278 + 99.8 \times weight$$

The paired t-test was used to analyze data from the accuracy study to compare known volumes with respective volumes measured by $N_2$ washout. p values that were less than 0.05 were regarded as significant.

Results

Patients Study:

Corrected for weight, the mean RV was 21.3 ml/kg (CI 18.7, 24.0 ml/kg) and, after correction for switching errors above FRC, the mean FRC was 25.5 ml/kg (CI 22.8, 28.1). In each of the nine infants, the difference between the mean FRC and RV was statistically significant (unpaired t-test, p<0.05). In addition, RV and FRC measurements did not overlap. FIGS. 2A, B, C are graphs of the mean (SD [T]) of residual volume (RV) [◊] and functional residual capacity Slopes of mean RV and FRC regression lines were significantly different from zero (P<0.01) but the differences between the lines' slopes were statistically insignificant (P>0.30). Nevertheless, the differences between RV and FRC lines intercepts were statistically significant for height (p=0.025) and weight (p=0.048) but not for age (p=0.065) (Table 2). In each patient, RV measurements were reproducible, mostly within 5% and in five patients, 2% (FIG. 2). In four subjects, a higher $P_j$ by 10 cm $H_2O$ did not produce a lower RV. The mean percent predicted FRC in the study was 114 (CI 104, 125) based on the collated data from healthy children (Table 1).

How was it confirmed that the lungs were at residual volume when the slide valve switched the infant into pure oxygen?

This was achieved by analyzing the signals collected on the CCCS computer. FIGS. 3A–3D are traces of flow, volume, airway opening pressure ($P_{ao}$) and jacket pressure ($P_j$) from infant #6. In this illustration, inspiration is negative and expiration is positive. The infant is hyperventilated by occluding the expiratory limb of the Y-adapter (FIG. 1A). As the lung volume is raised in the infant, $P_{ao}$ rises to a plateau set at 30 cm $H_2O$ by the pressure relief valve. Close to the end of the fifth passive expiration, the jacket is activated, at 14.32 s, generating a positive small sharp peak on the expiratory flow limb signaling the onset of a forced expiratory flow. Note that at 16 s, flow and $P_{ao}$ are zero, but $P_j$ is 82 cm $H_2O$ indicating chest compression, i.e., lungs are at RV. A miniscule upward shift in $P_{ao}$ baseline, due to the slide valve switching the infant into the bias flow of $O_2$, can be noted at 16.2 s (see also FIGS. 6A–6D for a zoomed view of this trace).

FIGS. 4A–4D, 5A–5D and 6A–6D are illustrations from patients (pt) 2, 7, and 6, respectively, and zoom on the time period that begins with jacket inflation and ends at the $20^{th}$ second of the data collection period. Each includes a trace of flow, volume, airway opening pressure ($P_{ao}$), and jacket pressure ($P_j$). In these illustrations, inspiration is negative and expiration is positive. Jacket inflation causes a sharp rise in flow (forced expiration) and a simultaneous miniscule rise in $P_{ao}$ followed by a rapid return to zero. Note in each $P_{ao}$ tracing the abrupt upward shift in baseline from zero to about 0.65 cm $H_2O$ caused by the switching of the infant into the bias flow of oxygen. Note also a zero flow and a raised $P_j$ plateau at the time of the switching. Note that after switching the infant into $O_2$, he no longer breathes through the pneumotachometer. The rapid $P_j$ decline which signals jacket deflation leads to a synchronous negative deflection in $P_{ao}$ due to the outward springing of the compressed infant's chest generating this negative airway pressure. $P_{ao}$ then resets and remains at 0.65 cm $H_2O$ signaling apnea (FIGS. 4A–4D and 5A–5D). This post-expiratory pause is followed, in FIGS. 5A–5D, by a negative deflection (inspiration) in $P_{ao}$ followed by a subsequent rise to 1.35 cm $H_2O$ (expiration). No significant post-expiratory pause is observed after jacket deflation in FIGS. 6A–6D. The negative $P_{ao}$ of the outward chest recoil is immediately followed by a large negative deflection (inspiration) then a rise to 0.78 cm $H_2O$ (expiration) (FIGS. 6A–6D). Note the return of $P_{ao}$ to 0.65 cm $H_2O$ at 19.4 s, indicating the lack of significant chest wall excursions (FIGS. 6A–6D).

For all RV measurements in this study, further zooming was performed on the period that began with jacket inflation and ended at the $20^{th}$ second of the data collection period. This enabled us to establish the three criteria for an acceptable measurement (see above) and determine the exact time of slide valve activation. After activating the slide valve, the infant was no longer breathing through the pneumotachometer (FIG. 1B) and the $P_{ao}$ signal provided additional information. In FIGS. 4A–4D (pt 2), F and $P_{ao}$ have reached zero at 16.050 s; activation of the slide valve at 16.945 s led to an abrupt -over 0.04 s- upward shift of 0.66 cm $H_2O$ in the baseline of $P_{ao}$. This was due to the infant being switched into the constant bias flow of $O_2$ which generated this continuous positive $P_{ao}$ of 0.66 cm $H_2O$. This positive $P_{ao}$ was observed in every RV measurement in all nine patients. Further confirmation was obtained by briefly interrupting the $O_2$ bias flow, which then abolished this positive $P_{ao}$ (data not shown). Thus, a time reference point for valve activation could be precisely determined. In FIGS. 4A–4D, the period between the activation of the valve at 16.945 s and the end, at 17.250 s, of the $P_j$ plateau (82.4 cm $H_2O$) was 0.305 s. Jacket deflation, which started at 17.250 s, led to a synchronous and rapid -over 0.275 s- negative deflection of 0.46 cm $H_2O$ in $P_{ao}$. This was presumably due to the outward springing of the chest wall, which was compressed by the jacket, causing the airway pressure to become more negative than the ambient pressure resulting in passive indrawing of gas ($O_2$ from the bias flow) into the airways of the apneic infant. While apnea continued, the bias flow of $O_2$ slowly, over 0.70 s, increased $P_{ao}$ back to its 0.66 cm $H_2O$ level. The total duration of this negative deflection was 0.975 s. After complete jacket deflation, post-expiratory apnea lasted at least 2.0 s in this infant (FIGS. 4A–4D).

In FIGS. 5A–5D (pt7), the negative deflection in $P_{ao}$ from the chest wall recoil was followed by apnea lasting 7.02 s. Then, a small negative deflection of a shallow inspiration starting at 17.82 s was followed by a larger inspiration at 18.675 s. The subsequent overshooting of $P_{ao}$ above baseline was presumably due to a continued expiration into the bias flow of $O_2$ raising $P_{ao}$ above baseline. No significant post-expiratory pause was noted in FIGS. 6A–6D (pt 6). The negative deflection of the outward chest recoil was followed by a large negative deflection caused by the patient's early inspiration that started at 17.45 s with a subsequent overshooting of $P_{ao}$ (expiration).

FIGS. 7A and 7B include traces of $P_{ao}$ and $P_j$ from pt 3. It zooms on the period between the switching into oxygen and ends at the $20^{th}$ second. At the time of the switching, $P_{ao}$ is zero -flow is also zero (not shown)- and $P_j$ is 64.7 cm $H_2O$. Note the lack of a significant post-expiratory pause. The negative deflection in $P_{ao}$ caused by the outward springing of the chest wall, begins at 14.1 s and merges at 14.3 s with an early more negative deflection (inspiration) followed by increasingly larger negative $P_{ao}$ deflections indicating progressively larger tidal inspirations. This patient had a respiratory rate of 54 per min.

FIGS. 7A and 7B (pt 3), the outward chest recoil induced a small negative deflection in $P_{ao}$ which merged with another more negative deflection of an early inspiration. Progressively larger negative deflections in $P_{ao}$ indicated progressively larger tidal inspirations. This patient had respiratory rate of 54 per min. Inspiratory efforts were simultaneously confirmed by observing the collapsible breathing bag.

Figure 8:
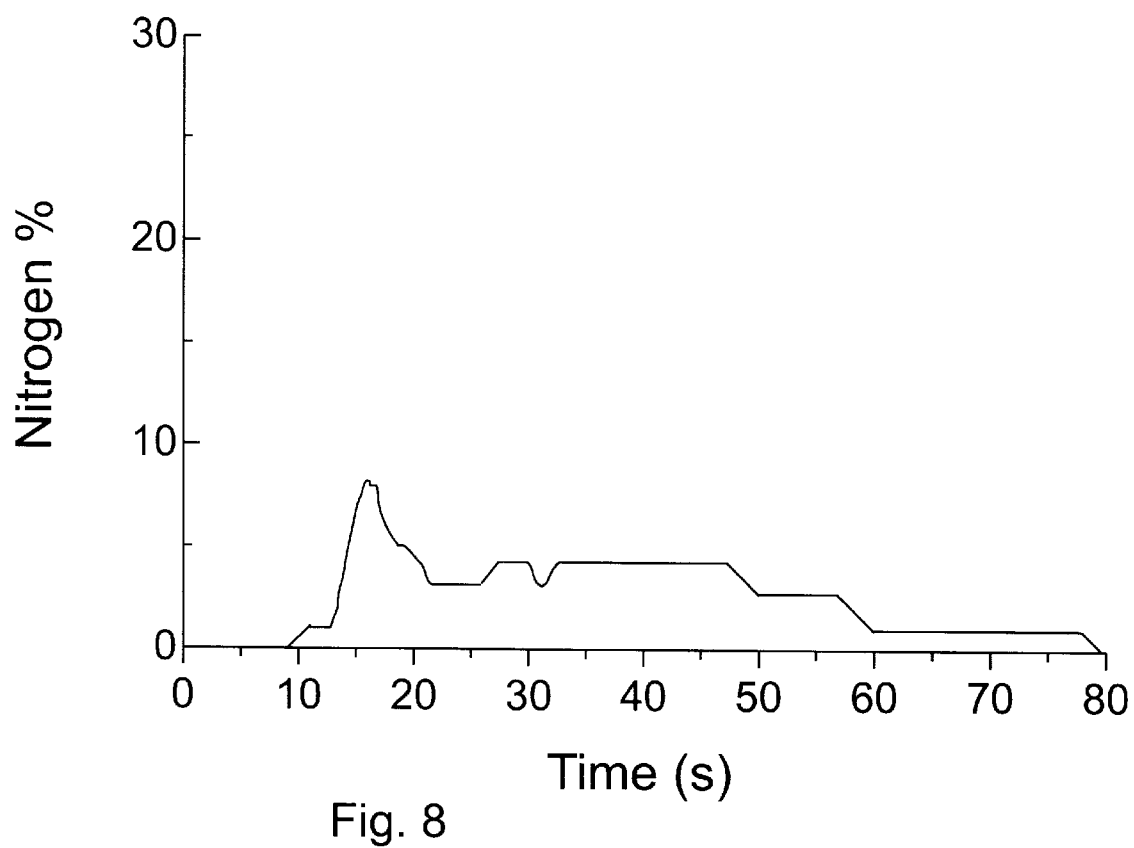
FIG. 8 is a graph showing the nitrogen washout curve of residual volume.

FIG. 8 illustrates the nitrogen washout curve of residual volume. Note the curve rises above baseline after a latent period (9 s). The initial peak and the area under the curve are smaller than those of FRC (not shown) in the same subject.

The mean period between the switching to $O_2$ and the end of $P_j$ plateau was 0.301 s (CI, 0.211, 0.391). Typically, the RV $N_2$ washout curve rose above baseline 10–15 s, vs. 1 s for FRC, after the slide valve switched the infant into pure $O_2$ (FIG. 8). It had a peak and an area under the curve (INS) that were smaller than those of FRC in the same subject. The mean washout duration for RV was longer than FRC: 80.9 s (CI 71.3, 90.4) vs. 72.4 s (CI 64.9, 79.8) (p<0.001). The intrasubject washout duration was mostly within 10 s.

Figure 9A:
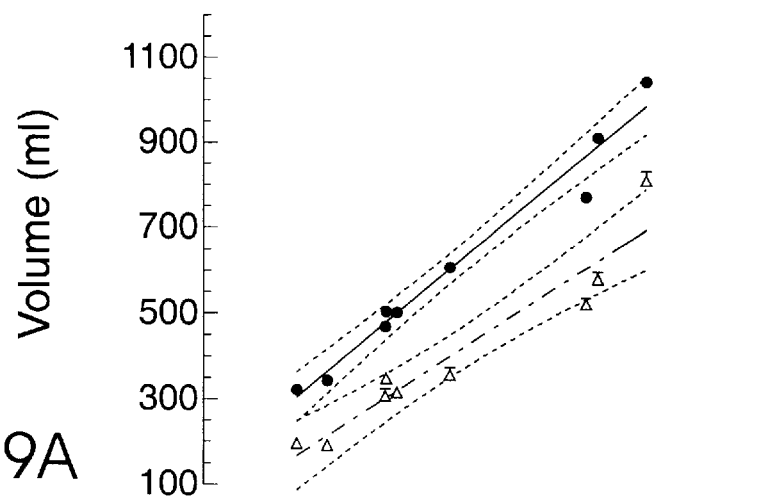
FIGS. 9 A, B, C are graphs of the mean (SD [T]) of forced vital capacity (FVC) [Δ] and mean total lung capacity at a raised lung volume to an airway opening pressure of 30 cm $H_2O$ ($TLC_{30}$) [•] from each infant plotted against the respective height, weight and age. The straight dashed and solid lines are FVC and $TLC_{30}$ regression lines, respectively. The curved dotted lines represent the 95% confidence limit.
Figure 9B:
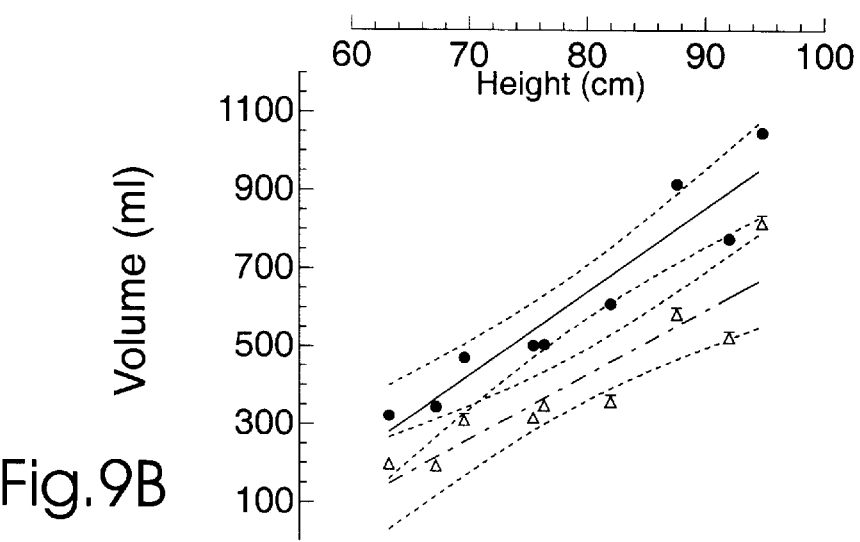
Figure 9C:
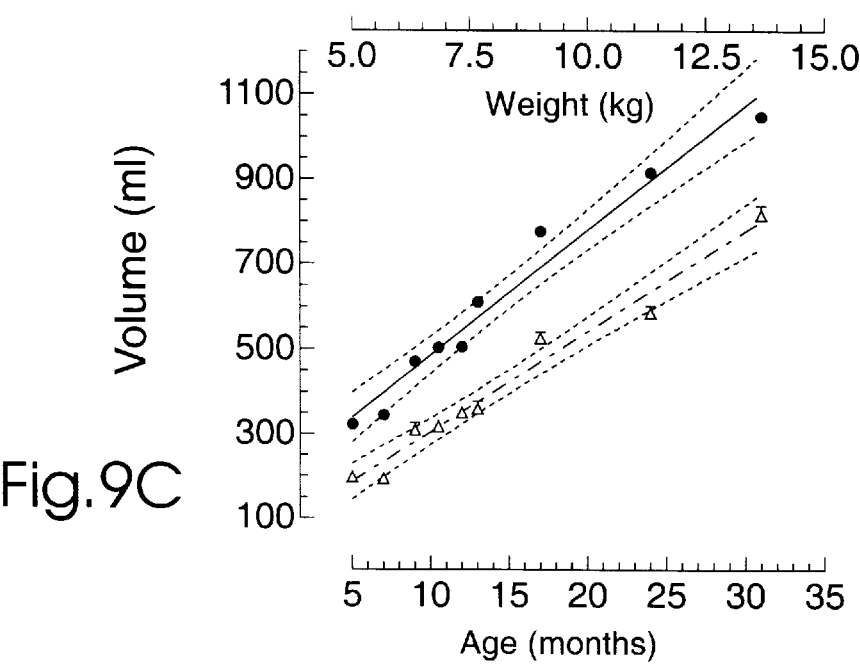

FIGS. 9 A, B, and C illustrates the mean (SD [T]) of forced vital capacity (FVC) [Δ] and mean total lung capacity at a raised lung volume to an airway opening pressure of 30 cm $H_2O$ ($TLC_{30}$) [•] from each infant are plotted against the respective height, weight and age. The straight dashed and solid lines are FVC and $TLC_{30}$ regression lines, respectively. The curved dotted lines represent the 95% confidence limit.

Corrected for weight, the mean FVC was 40.2 ml/kg (CI 33.0, 47.3) and $TLC_{30}$, 61.5 ml/kg (CI 54.4, 68.7). FVC and $TLC_{30}$ exhibited a strong age, height and weight dependence as indicated by the coefficient of determination ($r^2$) (Table 2, FIGS. 9A–9C). The mean percent predicted $TLC_{30}$ was 90% (CI 81, 99) (Table 1).

Accuracy Study with the Lung Model

Results from this in vitro study are presented in Table 3.

TABLE 3

Accuracy Study - Measurement of Known Air Volumes by Nitrogen Washout

| Known Volume (ml) | Measured Volume (ml) | Error (%) |
|---|---|---|
| 42 | 41.8 (0.4)† | −0.47 |
| 92 | 92.2 (0.6) | 0.22 |
| 142 | 141.9 (1.1) | −0.07 |
| 192 | 191.1 (1.2) | 0.46 |
| 242 | 242.4 (1.9) | −0.16 |

TABLE 3-continued

Accuracy Study - Measurement of Known Air Volumes by Nitrogen Washout

| Known Volume (ml) | Measured Volume (ml) | Error (%) |
| --- | --- | --- |
| 292 | 290.9 (1.4) | −0.37 |
| 342 | 341.6 (1.8) | −0.11 |
| 392 | 391.9 (2.6) | −0.02 |
| 442 | 442.8 (2.9) | −0.18 |
| 492 | 490.4 (1.4) | −0.32 |
|  |  | −0.10 (0.28)* |

†Values are mean (sd) of five measurements performed randomly over a fourteen-hour period.
*Mean (sd)

The mean coefficient of variation (CV) of all volumes was 0.66%. The mean difference between measured and known volumes was 0.30 ml (CI −0.18, 0.79 ml). This difference was not statistically significant (p=0.22). The mean percentage error was −0.1% (range, −0.47 to 0.46%).

Figures 10A, 10B, 10C, 10D:
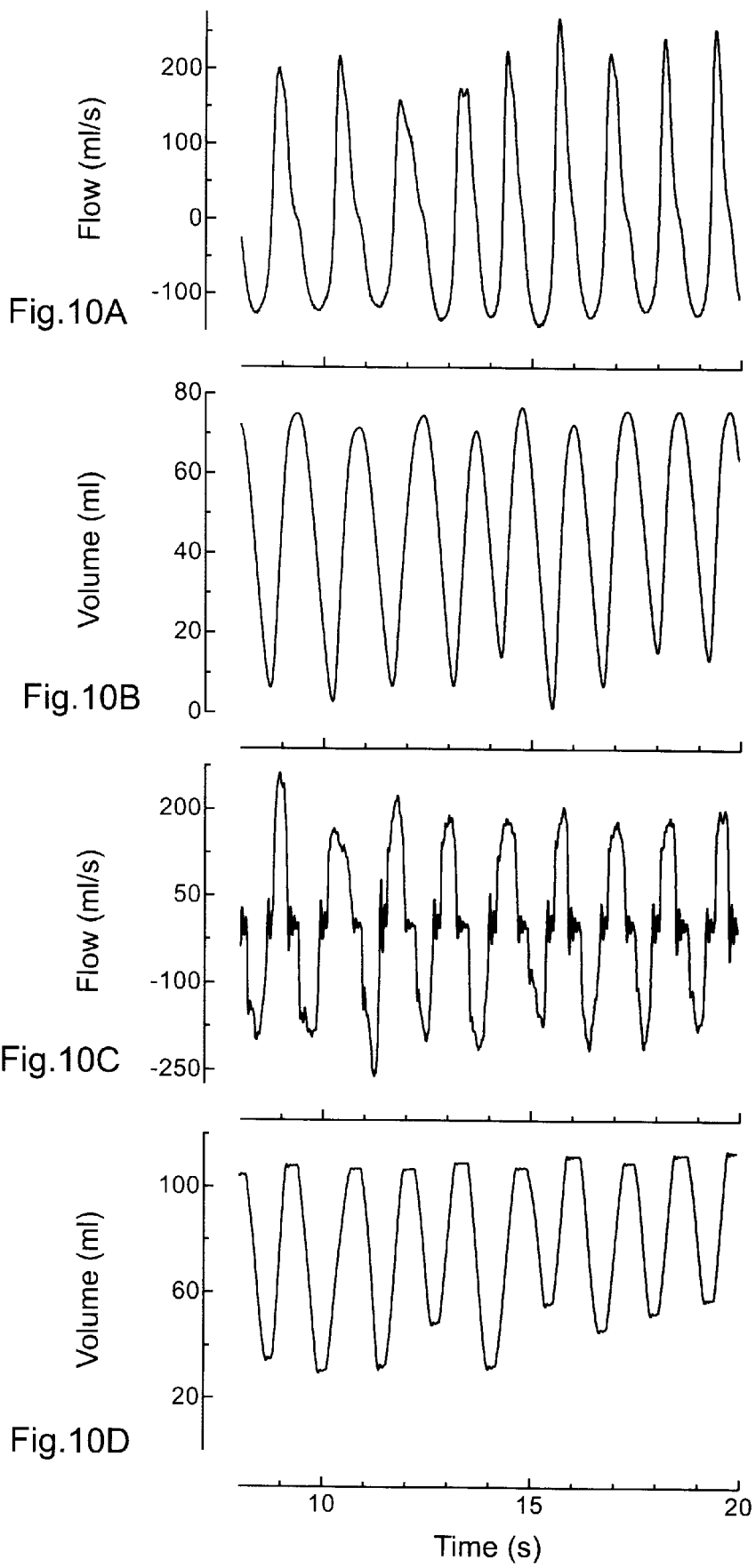
FIGS. 10A–10D shows four graphs illustrating the influence of the collapsible breathing bag (BB) on gas flow in the $N_2$ mixing chamber during in vitro washout. The flow and volume signal patterns, respectively, are compared using a pneumotachometer connected to the outlet of the $N_2$ mixing chamber, before (FIGS. 10C and 10D) and after (FIGS. 10A and 10B) the BB was introduced in the washout circuit. Note the presence of flow transients in the absence of BB.

FIG. 10 shows the influence of the collapsible breathing bag (BB) on gas flow in the $N_2$ mixing chamber during in vitro washout. Using ~70 ml stroke volumes from the calibrating syringe to simulate tidal breathing, we compared flow and volume signals pattern, using a pneumotachometer connected to the outlet of the $N_2$ mixing chamber, before (lower two panels) and after the BB was introduced in the washout circuit. Note the presence of flow transients in the absence of BB.

The BB had a clear influence on the flow and volume signals waveform in vitro. In the absence of the BB, flow transients were frequent (FIGS. 10A–10D).

Discussion

All patients remained clinically stable throughout the study. Using the technique described in this manuscript, in each of the nine infants with cystic fibrosis, not only was the mean RV lower than FRC (p<0.05), but also RV and FRC measurements did not overlap. RV measurements were very reproducible, mostly within 5%, and in five patients, 2%. Hence, contrary to FRC, RV appears to be a reliable volume landmark. During the brief inhibition of the infant's respiratory drive, RV would unlikely be affected by dynamic events such as sleep state, dead space or airway caliber. Any measurement of FRC is, however, a measurement of dynamic FRC.

In performing the RV maneuver, we chose to trigger jacket inflation late in passive expiration, during the brief inhibition of the infant's respiratory drive, for three reasons. First, to ensure complete exhalation to residual volume when the slide valve was switched. Second, to allow the operator a reasonable time to react and sequentially activate jacket inflation and the slide valve in a timely fashion. Third, activating jacket inflation at a lower rather than a higher lung volume has the theoretical advantage of minimizing air trapping so that more reproducible measurements of RV would be obtained. It has been suggested that RV is closer to FRC in infants than in older children. Hence, we had thought that even the induction of a partial forced expiration in these patients who probably had some small airway disease, might cause an early closure of small airways with increased air trapping and an inability of our methodology to discriminate between RV and FRC measurements. Clearly, that was not the case. Indeed, Patient 6 had a significant airway obstruction as indicated by a concave pattern of the flow limb of the flow-volume curve (data not shown) and had the highest percent predicted FRC (138%) (Table 1). In this patient, RV measurements remained reproducible and did not overlap with those of FRC. Moreover, the two RV measurements were within 5% despite a difference of 15 s between washout times.

A negative deflection in $P_{ao}$ occurred synchronously with jacket deflation. It was observed in every RV measurement in all patients and was ascribed to the outward springing of the chest wall that was compressed by the jacket. It was even noticed in patient 3 who was tachypneic and had reproducible RV measurements (FIGS. 7A and 7B).

A study on 11 healthy infants reported a mean $N_2$ washout time of 59 s (range, 35 to 90 s) for FRC. In another study of wheezy infants recovering from bronchiolitis, the washout time was shorter, 50 s (range, 30 to 75). One would expect to find a longer washout time in the presence of airway obstruction because of the slow equilibration of trapped $N_2$ rich gas with the pure $O_2$, as was the case in our patients with CF (mean, 72.4; range, 49 to 97). Differences might be due to a different underlying disease process, CF vs. recovery from bronchiolitis, the subject's respiratory rate and tidal volume which in turn could be influenced by sedation, or testing conditions such as the background flow of $O_2$. Conceivably, a relatively high as opposed to a low flow of $O_2$ could shorten the washout time. We used a fixed flow rate of 10 L/min for all patient tests. Indeed, the intrasubject washout time in our study had no influence on the reproducibility of measured washout volumes. It seemed unlikely that washout volumes were overestimated because of additional release of $N_2$ from the blood and tissues. We think that RV washout times were longer than FRC's due to the induced apnea and the subsequent resumption of breathing with small tidal volumes (FIGS. 4A–7B). Similarly, the $N_2$ washout curve of RV had a smaller peak and area under the curve (INS) than FRC's because of the initial small tidal volumes following the apnea and the inherently smaller volume of RV (FIG. 8).

While measuring lung volume has been regarded as physiologically and clinically important, accurate measurement is undoubtedly equally important. Studies employing the PPU have occasionally explored the accuracy of the $N_2$ washout technique and possible sources of errors. Indeed, a recent study comparing lung volume measurements by whole body plethysmography and $N_2$ washout reported a lack of accuracy and reliability of the two techniques in infants with airway obstruction and concluded that no "gold standard" technique was available for use in this setting (Eber E, Steinbrugger B, Modl M, et al. Lung volume measurements in wheezy infants. comparison of plethysmography and gas dilution. Eur Respir J 1994; 7, 1988–94.). The PPU is a widely used system in infant pulmonary function laboratories. The system can be mobilized to perform bedside measurements. The dead space and apparatus resistance are low in the open $N_2$ washout, making it suitable for small or sick infants. The author has performed a painstaking systematic exploration of possible sources of error when using the $N_2$ washout. Potential sources of error, suggested or reported, included changes in background oxygen, the infant's peak flow exceeding the background flow, a change in calibration over time, or leaks in the circuit, including the face mask, and in infants with airway obstruction, the unanswered question of the final $N_2$ concentration, length of the washout time and the minimal time interval between consecutive measurements. Over 2000 in vitro washouts were performed using the calibrating syringe as a lung model. Furthermore, we performed simulations: we used unequal stroke volumes and different rates with the calibrating syringe to simulate periodic breathing, sighs, rapid shallow breathing, pauses to simulate apneas or temporary upper airway obstruction (M G Morris, unpublished data). Of several connections, equipment warming times, flow rates of the background $O_2$, the methodology described in detail in this manuscript yielded the best reproducible results. The $N_2$ washout circuit can be quickly assembled into a virtually leak-free unit that can be disinfected in between patient testing.

The incorporation of the collapsible breathing bag in the $N_2$ washout circuit had a profound stabilizing effect that led to an exceptional reproducibility in vivo and accuracy in vitro in measured washout volumes. The in vitro study indicated that flow transients were more frequent in the absence of the BB (FIGS. 10A–10D). To ensure that the observed waveform difference was not the result of a technical variation in injecting air from the calibrating syringe, we computed tidal breathing indices, namely the tidal volume, the inspiratory, expiratory and total time as well as the frequency (VT, tI, tE, ttot, and f (Hz), respectively) from this in vitro study. Using the unpaired t test, we found no significant difference between indices' means, before and after the BB was placed in the circuit (data not shown). Given the low resistance in the open circuit of $N_2$ washout, we think that the BB acted as a buffer reservoir that prevented large swings in the bias flow of $O_2$ in the $N_2$ mixing chamber. These swings inevitably occurred during the breathing cycle of an older child who had a large tidal volume. More importantly, BB minimized the retrograde movement of mixed $O_2$ and $N_2$ gas after it had passed beyond the sampling needle port. The latter explanation was supported by the observation that when a relatively short tube, instead of our 1.8 m one, was attached to the $N_2$ mixing chamber's outlet port, a sharp rise above baseline of the $N_2$ washout curve would occur when an older child took a deep sigh breath. This was presumably due to the retrograde movement of gas enriched with room air $N_2$ into the outlet port and through the sampling needle. An In vitro simulation, using a sharp pull on the piston of the calibrating syringe, lent support for this hypothesis. The BB served also as a constant monitor for tidal breathing. In the author's experience, an occasional transient upper airway obstruction in the sedated infant was easily detected and promptly corrected during washouts. Pauses during periodic breathing were also noted. If either of these two phenomena were to occur close to the end of a washout, they could conceivably lead to a premature return of the $N_2$ washout curve to baseline and termination of the test by the operator resulting in an underestimation of the measured washout volume. A substantial or near-complete deflation of the BB during a washout by the inspiring child could presumably alert the operator to the possibility of a peak inspiratory flow exceeding the bias flow of $O_2$. This has not occurred in this study. The insertion of a pneumotachygraph between the face mask and the mouth port of the slide valve could provide an alternative continuous monitoring for tidal breathing during washouts. However, this has the disadvantage of increasing the dead space and the resistance of the washout circuit without providing the buffering capability of the BB for large tidal volumes. Taken together, we think that the BB should be an integral component of the open $N_2$ washout circuit. The location of the BB in the circuit was best between the patient and the $O_2$ source and closer to the former. Placement distal to the patient tended to retain some of the washed out $N_2$ and unless the bag was slowly and completely squeezed just before the washout was completed, measured volumes would be underestimated (M. G. Morris, unpublished data).

Adequate equipment warming time was an important factor in performing reliable $N_2$ washouts. Hanging the needle valve for at least 45 minutes to sample room air was determined to be essential to achieve a stable $N_2$ concentration reading in our system. Premature termination of this step contributed to the change in $N_2$ calibration over time and with the finding, after patient testing had been completed, of a $N_2$ concentration below 79% when the needle sampled room air again.

Drifting of the baseline has been a major challenge during testing and a potential source for a systematic error by overestimating measured washout volumes. Hence, frequent checks for baseline drifts and correction were essential to obtain reproducible data. Interestingly, drifting might not occur for 60 s, but then the INS starts rising rapidly. Hence, in testing patients with airway obstruction, testing for drifts up to 90 s was important because of the expected prolonged washout times. In our study the ranges of washout times for RV and FRC were 56 to 112 and 54 to 90 s, respectively. An immediate rise above baseline of the $N_2$ washout curve after the slide valve was switched indicated the presence of a drift if air had not yet entered the bias flow of $O_2$ from either the calibrating syringe or the apneic infant during RV measurement. A true rise in INS was noted when a relatively short tube, as opposed to our 1.8 m corrugated tube, was attached to the mixing chamber outlet port allowing room air to diffuse back into the port and sampling needle. Another potential source was a discontinuity in any of the various connections, and that happened only once through a visible break in the aerosol 'T' connection port. Interestingly, during an in vitro experiment, an accidental tear in the collapsible bag caused a paradoxical decrease in the calculated washout volume. This was ascribed to a ball valve mechanism that either allowed injected $N_2$ from the calibrating syringe to escape but prevented room air from entering the $O_2$ stream, or caused a change in the flow of $O_2$ because the gas had escaped through the tear when the breathing bag inflated. In our experience, we think that inadequate warming time of the PPU and drifting of the baseline of the $N_2$ washout curve were the two main causes for a change in calibration over time that we and others had observed. Changes in the background flow of $O_2$ were presumed to have caused an observed change in $N_2$ calibration over time in a previous study, necessitating the use of a correction factor after patient testing had been completed. This was not noted in our study and no correction factor needed to be applied on any test result.

It has been suggested that the lung volume may be lowered by breathing high oxygen concentrations (Geubelle F, Francotte M, Beyer M, et al. Functional residual capacity and thoracic gas volume in normoxic and hyperoxic newborn infants. *Acta Paediatr Belg* 1977; 30, 221–5.). This was not observed in the present study where each infant had had reproducible RV and FRC measurements, or in a previous study on healthy subjects. Our waiting periods in between measurements, were at least twice the washout time. This seemed to have been an adequate period for the initial fractional alveolar $N_2$ concentration (0.79) to be restored since RV and FRC were similarly reproducible in those few instances when we had waited longer.

Using the calibrating syringe as a lung model, the author has used a wide range of volumes for several two-point calibration experiments. These in vitro experiments suggested that the system remained linear for at least 50 ml beyond the two-point calibration. We chose 42 and 342 ml for all patient tests so that we would become familiar with their respective INS and easily detect aberrant numbers. This added a quality assurance element to our operating conditions. The use of a small volume (42 ml) has the advantage of shortening the calibration time.

The application of a face mask to the infant's face may significantly reduce the dead space within the mask (Sly P D, Davis G M. Equipment requirement for infant respiratory function testing. In: J Stocks, P D Sly, R S Tepper, W J Morgan (eds): *Infant Respiratory Function Testing*. New York: John Wiley & Sons, Inc, 1996: 45–80.). The actual combined dead space of size 1 clear face mask with its connected slide valve mouth port was found to be 23 ml. Patient 8 had the smallest effective dead space of 8 ml. The actual combined dead space of the connected ports of the face mask and slide valve was 8 ml. This clearly seemed to be an obligatory dead space because it was unlikely for it to be penetrated by the infant's nose, lips or cheeks. We think that previously reported dead spaces in the literature were probably underestimated.

In the present study, a 0.05 s airway occlusion was used during the performance of RVRTC to prevent any significant lung volume loss prior to maximal inflation of the jacket. More importantly, it also completely prevented leaks around the mask that occurred with longer occlusions because of increasing pressure in the mask, which was the highest during the occlusion. The mean FVC from $V_{30}$ in our CF patients was 40.2 ml/kg (range, 28.3–49.1 ml/kg) which is slightly less than the reported value in the literature of 46.1 ml/kg (range, 27.2–61.5 ml/kg) for newborn infants, obtained by the forced deflation technique (FD) (LeSouef P N, Castile R, Turner D J, et al. Forced expiratory maneuvers. In: J Stocks, P D Sly, R S Tepper, W J Morgan (eds). *Infant Respiratory Function Testing*. New York: John Wiley & Sons, Inc, 1996: 379–409.). This could be due to the CF in our patients and the pressures used to generate FVC by FD (+40 cm $H_2O$ to −40 cm $H_2O$). Using a prediction equation derived from a previous study on intubated patients without an underlying lung disease, the mean per cent predicted $TLC_{30}$ of our infants with CF was 90% (CI 81, 99). However, there are differences in testing conditions such as the use of anesthesia and muscle paralysis, which influence pressure-volume relations, vs. sedation in our study. Since FVC may be smaller than a slow vital capacity in obstructive airway disease, it is possible that a small TLC was obtained in some of our patients because we used FVC (Hyatt R, Scanlon P D, Nakamura M. *Interpretation of pulmonary function tests-A practical guide*. Philadelphia: Lippincott-Raven, 1997:31.).

In the present study, RV, FRC, FVC and $TLC_{30}$ correlated with the age, height and weight of patients (FIGS. 2 and 9; Table 2). A previous study found no correlation between age and thoracic gas volume or maximal expiratory flow at functional residual capacity in a group of infants with CF (Beardsmore C S, Bar-Yishay E, Maayan C, et al. Lung function in infants with cystic fibrosis. *Thorax* 1988; 43, 545–51.).

In two patients, chloral hydrate and hydroxyzine had a synergistic sedative effect. Dentists have used this drug combination for minor procedures in the pediatric population. We have successfully used it in our laboratory, especially in older children, up to three years of age, in whom the maximum dose of chloral hydrate had been ineffective. Further studies are needed to confirm the usefulness of this drug combination in infant lung function testing.

In conclusion, we have developed a noninvasive technique that could be used for routine measurement of the residual volume by nitrogen washout in infants. In each infant, measurements of RV and FRC were reproducible and did not overlap even in the presence of a significant airway obstruction or tachypnea. Measured variables correlated with the infant's age, height and weight. We postulate that besides FVC and forced expiratory flows measured by RVRTC, FRC, RV and $TLC_{30}$ measurements as well as the $RV/TLC_{30}$ ratio will be useful variables in prospective studies, by providing a comprehensive assessment of the infant lung in health and disease.

What is claimed is:

1. A method of measuring residual lung volume (RV) in an infant, comprising the steps of:
    (a) hyperventilating the infant by raising lung volume to a predetermined airway opening pressure until the respiratory drive is inhibited,
    (b) triggering rapid thoracoabdominal compression using an inflatable squeeze jacket on the infant before the end of the last passive expiration to induce a forced expiration down to the residual volume (RV),
    (c) maintaining thoracoabdominal compression during the pause in spontaneous respiration after the end of said last passive expiration while said respiratory drive is inhibited,
    (d) switching the infant's inspired air to 100% oxygen if using nitrogen washout or to a gaseous mixture containing a known concentration of an inert gas before the decline of the jacket pressure plateau and when the airflow and airway opening pressure are both zero,
    (e) terminating thoracoabdominal compression,
    (f) upon the resumption of spontaneous respiration by the infant, measuring the volume of the remaining gas in the infant's lungs by inert gas washout or dilution to calculate residual volume (RV).

2. The method of claim 1 comprising the further step of smoothing out flow transients in the infant's respiration following resumption of spontaneous respiration using a collapsible breathing bag.

3. The method of claim 1 wherein said predetermined raised airway opening pressure is around 30 cm $H_2O$.

4. The method of claim 1, comprising the further steps of determining the functional residual capacity (FRC) and calculating the expiratory reserve volume as the difference between the functional residual capacity (FRC) and the residual volume (RV).

5. A method of measuring both forced vital capacity (FVC) and residual lung volume (RV) in one breath in an infant, comprising the steps of:
    (a) hyperventilating the infant by raising the lung volume to a predetermined airway opening pressure until the respiratory drive is inhibited,
    (b) with the last inhalation, the lung volume being raised to the predetermined airway opening pressure, triggering rapid thoracoabdorninal compression using an inflatable squeeze jacket on the infant to generate a forced expiration down to residual volume (RV),
    (c) measuring the forced vital capacity (FVC) as the volume of gas generated by this forced expiration from the raised lung volume down to residual volume (RV),
    (d) maintaining thoracoabdominal compression during the pause in spontaneous respiration after the end of said forced expiration while said respiratory drive is inhibited,
    (e) switching the infant's inspired air to 100% oxygen if using nitrogen washout or to a gaseous mixture containing a known concentration of an inert gas before the decline of the jacket pressure plateau and when the airflow and airway opening pressure are both zero, (f) terminating thoracoabdominal compression, (g) upon the resumption of spontaneous respiration by the infant, measuring the volume of the remaining gas in the infant's lungs by inert gas washout or dilution to calculate residual volume (RV).

6. The method of claim 5 comprising the further step of smoothing out flow transients in the infant's respiration following the resumption of spontaneous respiration using a collapsible breathing bag.

7. The method of claim 5 wherein said predetermined raised airway opening pressure is around 30 cm $H_2O$.

\* \* \* \* \*